US006369221B1

(12) United States Patent
Hardy et al.

(10) Patent No.: US 6,369,221 B1
(45) Date of Patent: Apr. 9, 2002

(54) THIAZOLOBENZOHETEROCYCLES, PREPARATION AND MEDICINES CONTAINING SAME

(75) Inventors: Jean-Claude Hardy, Cergy Saint Christophe; Jean Bouquerel, Drancy; Patrick Nemecek, Thiais; Jean-François Peyronel, Palaiseau, all of (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 09/484,836

(22) Filed: Jan. 18, 2000

Related U.S. Application Data

(63) Continuation of application No. PCT/FR98/01638, filed on Jul. 24, 1998.

(30) Foreign Application Priority Data

Jul. 28, 1997 (FR) .............................. 97 09556

(51) Int. Cl.⁷ .................. C07D 498/00; C07D 513/00; C07D 243/24; C07D 223/14; C07D 223/16
(52) U.S. Cl. ....................... 540/497; 540/504; 540/512; 540/548; 540/552; 540/560; 540/567; 540/573; 540/586; 540/593; 514/211.09; 514/211.1; 514/213.01; 514/214.01; 514/220; 514/221
(58) Field of Search .................. 540/497, 548, 540/560, 586, 504, 552, 573, 593, 512, 567; 514/211.09, 211.1, 213.01, 214.01, 220, 221

(56) References Cited

U.S. PATENT DOCUMENTS

| 3,794,646 A | * | 2/1974 | Welstead et al. | ......... 260/239.3 |
| 3,850,948 A | * | 11/1974 | Coffen et al. | ............ 260/306.7 |
| 3,857,854 A | * | 12/1974 | Hester, Jr. | .................... 260/307 |
| 4,107,303 A | * | 8/1978 | Aldrich et al. | .............. 424/244 |
| 4,218,448 A | * | 8/1980 | Aldrich et al. | .............. 424/244 |
| 5,008,280 A | * | 4/1991 | Gueremy et al. | ........... 514/367 |
| 5,401,737 A | * | 3/1995 | Sato et al. | .................. 514/220 |
| 5,461,048 A | * | 10/1995 | Sato et al. | .................. 514/211 |

FOREIGN PATENT DOCUMENTS

| EP | 0374040 | | 6/1990 |
| GB | 1173701 | * | 3/1968 |

OTHER PUBLICATIONS

International Preliminary Examination Report For PCT/FR98/01638, 1999.
Madge et al., The Metabotropic Glutamate Receptors, Annual Reports in Medicinal Chemistry, vol. 31, pp. 31–40, 1996.*

* cited by examiner

*Primary Examiner*—Brenda Coleman
(74) *Attorney, Agent, or Firm*—Irving Newman

(57) ABSTRACT

Disclosed are thiazolobenzoheterocycles of the general formula

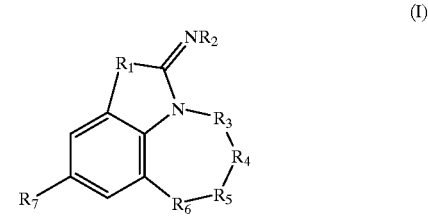
(I)

Including their isomers, racemates, enantioners and salts thereof, as well as processes for preparing these compounds and medicaments containing them. Also disclosed are novel intermediates for preparing the foregoing compounds, these intermediates having the formula

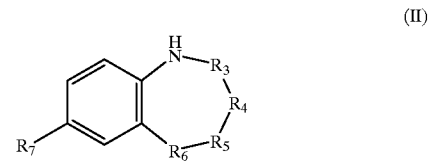
(II)

11 Claims, No Drawings

THIAZOLOBENZOHETEROCYCLES, PREPARATION AND MEDICINES CONTAINING SAME

CROSS-REFERENCE TO RELATED APPLICATIONS

This application is a continuation of International Application PCT/FR98/0138, filed Jul. 24, 1998.

The present invention relates to compounds of formula;

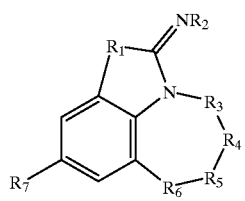

(I)

their isomers, racemates, enantiomers, their salts, processes for preparing them and the medicaments containing them.

In formula (I), $R_1$ represents a sulphur or selenium atom, $R_2$ represents a hydrogen atom or an alkyl radical, —$R_3$—$R_4$—$R_5$—$R_6$— represents a chain of formula

—$CH_2$—$CH_2$—$CH_2$—$CH_2$—, —$CH_2$—$CH_2$—$CH_2$—$CO$—,

—$CH_2$—$CH_2$—$CH_2$—$CH(R_8)$—, —$CH_2$—$CH_2$—$CH_2$—$Se$—,

—$CH_2$—$CH_2$—$Se$—$CH_2$—, —$CH_2$—$CH_2$—$CH_2$—$S$—,

—$CH_2$—$CH_2$—$CH_2$—$SO$—, —$CH_2$—$CH_2$—$CH_2$—$SO_2$—,

—$CH_2$—$CH_2$—$CH_2$—$O$—, —$CH_2$—$CH_2$—$CH_2$—$N(R_9)$—,

—$CH_2$—$CH_2$—$CO$—$CH_2$—, —$CH_2$—$CH_2$—$CH(R_8)$—$CH_2$—,

—$CH_2$—$CH_2$—$S$—$CH_2$—, —$CH_2$—$CH_2$—$SO$—$CH_2$—,

—$CH_2$—$CH_2$—$SO_2$—$CH_2$—, —$CH_2$—$C(alk)(alk')$—$S$—$CH_2$—, —$CH_2$—

$C(alk)$ $(alk')$—$SO$—$CH_2$—, —$CH_2$—$C(alk)$ $(alk')$—$SO_2$—$CH_2$—,

—$CR_2$—$CH$ $(R_{10})$—$S$—$CH_2$—, —$CH_2$—$CH$ $(R_{10})$—$SO$—$CH_2$—,

—$CH_2$—$CH$ $(R_{10})$—$SO_2$—$CH_2$—, —$CH_2$—$CH_2$—$O$—$CH_2$—,

—$CH_2$—$CH_2$—$N(R_9)$—$CH_2$—or —$CH_2$—$CO$—$N(R_9)$—$CH_2$—, $R_7$ represents a polyfluoroalkyl or polyfluoroalkoxy radical, $R_8$ represents a hydroxyl radical, $R_9$ represents a hydrogen atom or an alkyl or benzyl radical, $R_{10}$ represents an alkyl, —$CH_2OH$, —$COOalk$, —$COOH$ or —$CONH_2$ radical, alk represents an alkyl radical, alk' represents an alkyl radical.

In the preceding definitions and in those which will be given hereinafter, unless otherwise indicated, the alkyl radicals and portions contain 1 to 6 straight- or branched-chain carbon atoms.

Among the polyfluoroalkyl radicals, there may be mentioned the trifluoromethyl, 2,2,2-trifluoroethyl, 1,1,2,2-tetrafluoroethyl, perfluoroethyl, perfluoropropyl and perfluorobutyl radicals.

Among the polyfluoroalkoxy radicals, there may be mentioned the trifluoromethoxy, perfluoroethoxy, 2,2,2-trifluoroethoxy, 1,1,2,2-tetrafluoroethoxy, 2,2,3,3,3-pentafluoropropoxy, perfluoropropoxy and perfluorobutoxy radicals.

The preferred polyfluoroalkyl and polyfluoroalkoxy radicals are trifluoromethyl, trifluoromethoxy and pentafluoroethoxy radicals.

The invention also relates to the addition salts of the compounds of formula (I) with inorganic or organic acids.

The compounds of formula (I) which contain one or more asymmetric centres have isomeric forms; these isomers and mixtures form part of the invention. The racemates and the enantiomers of these compounds also form part of the invention.

The compounds of formula (I) for which $R_1$ represents a sulphur or selenium atom, $R_2$ represents a hydrogen atom, —$R_3$—$R_4$—$R_5$—$R_6$— represents a chain of formula —$CH_2$—$CH_2$—$CH_2$—$CH_2$—, —$CH_2$—$CH_2$—$CH_2$—$CO$—, —$CH_2$—$CH_2$—$CH_2$—$CH(R_8)$—, —$CH_2$—$CH_2$—$CH_2$—$Se$—, —$CH_2$—$CH_2$—$Se$—$CH_2$—, —$CH_2$—$CH_2$—$CH_2$—$S$—, —$CH_2$—$CH_2$—$CH_2$—$O$—, —$CH_2$—$CH_2$—$CH_2$—$N(R_9)$—, —$CH_2$—$CH_2$—$CO$—$CH_2$—, —$CH_2$—$CH_2$—$CH(R_8)$—$CH_2$—, —$CH_2$—$CH_2$—$S$—$CH_2$—, —$CH_2$—$C(alk)$ $(alk')$—$S$—$CH_2$—, —$CH_2$—$CH(R_{10})$—$S$—$CH_2$—, —$CH_2$—$CH_2$—$O$—$CH_2$—, —$CH_2$—$CH_2$—$N(R_9)$—$CH_2$— or —$CH_2$—$CO$—$N(R_9)$—$CH_2$—, $R_8$ represents a hydroxyl radical, $R_9$ represents a hydrogen atom or an alkyl or benzyl radical and $R_{10}$ represents an alkyl, COOalk or $CONH_2$ radical may be prepared by reacting an alkali metal thiocyanate or an alkali metal selenocyanate with a derivative of formula:

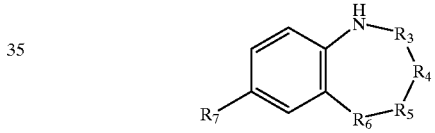

(II)

in which $R_7$ has the same meanings as in formula (I) and —$R_3$—$R_4$—$R_5$—$R_6$— represents a chain of formula —$CH_2$—$CH_2$—$CH_2$—$CH_2$—, —$CH_2$—$CH_2$—$CH_2$—$CO$—, —$CH_2$—$CH_2$—$CH_2$—$CH$ $(R_8)$—, —$CH_2$—$CH_2$—$CH_2$—$Se$—, —$CH_2$—$CH_2$—$Se$—$CH_2$—, —$CH_2$—$CH_2$—$CH_2$—$S$—, —$CH_2$—$CH_2$—$CH$ 2—$O$—, $CH_2$—$CH_2$—$CH_2$—$N(R_9)$ —, —$CH_2$—$CH_2$—$CO$—$CH_2$—, —$CH_2$—$CH_2$—$CH(R_8)$—$CH_2$—, —$CH_2$—$CH_2$—$S$—$CH_2$—, —$CH_2$—$C(alk)$ $(alk')$—$S$—$CH_2$—, —$CH_2$—$CH(R_{10})$—$S$—$CH_2$—, —$CH_2$—$CH_2$—$O$—$CH_2$—, —$CH_2$—$CH_2$—$N(R_9)$—$CH_2$— or —$CH_2$—$CO$—$N(R_9)$—$CH_2$—, $R_8$ represents a hydroxyl radical, $R_9$ represents a hydrogen atom or an alkyl or benzyl radical and $R_{10}$ represents an alkyl, COOalk or $CONH_2$ radical, alk and alk' represent an alkyl radical.

This reaction is generally carried out in the presence of bromine, chlorine, chloramide or copper(II) chloride, in an organic solvent such as acetic acid, at a temperature between 15° C. and the boiling point of the reaction medium. As alkali metal thiocyanate or alkali metal selenocyanate, it is preferable to use potassium thiocyanate or potassium selenocyanate.

The derivatives of formula (II) are new and, as such, form part of the invention.

The compounds of formula (I) for which $R_2$ represents an alkyl radical may be prepared by alkylation of a corresponding compound of formula (I) for which $R_2$ represents a hydrogen atom.

This alkylation is carried out by any method which makes it possible to alkylate an imine functional group. Preferably, the procedure is carried out by means of a derivative Ra-X in which Ra represents an alkyl radical and X represents a reactive group such as a halogen atom (preferably chlorine, bromine or iodine) or a tosyloxy radical, in an inert organic solvent such as an aliphatic alcohol (1–6C) (ethanol, propanol or butanol for example), a ketone (acetone or methyl ethyl ketone for example) or dimethylformamide, in the presence of a base such as an alkali metal carbonate (potassium carbonate for example), at a temperature between 20° C. and the boiling point of the reaction medium.

The compounds of formula (I) for which $R_2$ represents a hydrogen atom or an alkyl radical, $-R_3-R_4-R_5-R_6-$ represents a chain of formula $-CH_2-CH_2-CH(R_8)-CH_2-$ or $-CH_2-CH_2-CH_2-CH(R_8)-$ and $R_8$ represents a hydroxyl radical may also be obtained by reducing a corresponding compound of formula (I), for which $R_2$ represents a hydrogen atom or an alkyl radical and $-R_3-R_4-R_5-R_6-$ represents a chain of formula $-CH_2-CH_2-CO-CH_2-$ or $-CH_2-CH_2-CH_2-CO-$.

This reaction is carried out by any method which makes it possible to pass from a ketone to an alcohol. The procedure is generally carried out by means of sodium borohydride, in an alcohol such as methanol or ethanol, at a temperature of between 0 and 25° C.

The compounds of formula (I) for which $R_2$ represents a hydrogen atom or an alkyl radical and $-R_3-R_4-R_5-R_6-$ represents a chain of formula $-CH_2-CH_2-CH_2-SO-$, $-CH_2-CH_2-CH_2-SO_2-$, $-CH_2-CH_2-SO-CH_2-$, $-CH_2-CH_2-SO_2-CH_2-$, $-CH_2-C(alk)(alk')-SO-CH_2-$, $-CH_2-C(alk)(alk')-SO_2-CH_2-$, $-CH_2-CH(R_{10})-SO-CH_2-$ or $-CH_2-CH(R_{10})-SO_2-CH_2-$ may be prepared by oxidizing a corresponding compound of formula (I) for which the chain $-R_3-R_4-R_5-R_6-$ represents a chain of formula $-CH_2-CH_2-CH_2-S-$, $-CH_2-CH_2-S-CH_2-$, $-CH_2-C(alk)(alk')-S-CH_2-$ or $-CH_2-CH(R_{10})-S-CH_2-$.

This oxidation is carried out according to known methods of oxidizing sulphur-containing derivatives as described by M. HUDLICKY, Oxidations in Organic Chemistry, ACS Monograph, 186, 252–263 (1990). For example, the procedure is carried out by the action of an organic peracid or a salt of such an acid (percarboxylic or persulphonic acid, in particular perbenzoic acid, 3-chloroperbenzoic acid, 4-nitroperbenzoic acid, peracetic acid, pertrifluoroacetic acid, performic acid or monoperphthalic acid) or inorganic peracids or a salt of such an acid (for example periodic or persulphuric acid), in an inert solvent such as a chlorinated solvent (chloroform or dichloromethane for example), at a temperature of between 0 and 25° C. It is also possible to use hydrogen peroxide or a periodate (sodium periodate for example), in an inert solvent such as a lower aliphatic alcohol, water or a mixture of these solvents, at a temperature of between 0 and 20° C. It is also possible to carry out the procedure by means of tert-butyl hydroperoxide in the presence of titanium tetraisopropoxide or oxone$^R$ (potassium peroxymonosulphate) in a lower aliphatic alcohol or a water-alcohol mixture, at a temperature close to 25° C.

The compounds of formula (I) for which $R_2$ represents a hydrogen atom or an alkyl radical, $-R_3-R_4-R_5-R_6-$ represents a chain of formula $-CH_2-CH(R_{10})-S-CH_2-$ in which $R_{10}$ represents a radical $-CH_2OH$ may be prepared by reducing a corresponding compound of formula (I) for which $R_2$ represents a hydrogen atom or an alkyl radical, $-R_3-R_4-R_5-R_6-$ represents a chain of formula $-CH_2-CH(R_{10})-S-CH_2-$ in which $R_{10}$ represents a $-COOalk$ radical.

This reaction is carried out by any known method which makes it possible to obtain an alcohol from the corresponding ester. Preferably, the procedure is carried out by means of sodium borohydride, in an alcohol such as ethanol, at the boiling point of the reaction medium.

The compounds of formula (I) for which $R_2$ represents a hydrogen atom or an alkyl radical, $-R_3-R_4-R_5-R_6-$ represents a chain of formula $-CH_2-CH(R_{10})-S-CH_2-$ in which $R_{10}$ represents a $-COOH$ radical may be prepared by hydrolysing a corresponding compound of formula (I) for which $R_2$ represents a hydrogen atom or an alkyl radical, $-R_3-R_4-R_5-R_6-$ represents a chain of formula $-CH_2-CH(R_{10})-S-CH_2-$ in which $R_{10}$ represents a $-COOalk$ radical.

This reaction is carried out by any method which makes it possible to pass from an ester to the corresponding acid. Generally, the procedure is carried out by means of an alkali metal hydroxide (sodium hydroxide for example), in an inert solvent such as an alcohol (methanol or ethanol for example), at a temperature between 15° C. and the boiling point of the reaction medium.

The derivatives of formula (II) for which the chain $-R_3-R_4-R_5-R_6-$ represents a chain of formula $-CH_2-CH_2-CH_2-CH_2-$ and $R_7$ represents a polyfluoroalkyl or polyfluoroalkoxy radical may be obtained by reacting a 1,4-dihalobutane with the lithium derivative of a 4-polyfluoroalkylaniline or 4-polyfluoroalkoxyaniline whose amine functional group is protected, followed by deprotection of the NH.

This reaction is generally carried out in tetrahydrofuran, at a temperature of −78° C. It is preferable to protect the amine functional group in the form of a tert-butyl carbamate; in this case, the deprotection is carried out by means of trifluoroacetic acid, in an inert organic solvent such as a chlorinated solvent (chloroform or dichloromethane for example), at a temperature close to 20° C. Preferably, 1-chloro-4-iodobutane is used. The lithium derivative is obtained by reacting tert-butyllithium, in pentane, with 4-polyfluoroalkylaniline or 4-polyfluoroalkoxyaniline whose amine functional group is protected, in tetrahydrofuran, at a temperature of −78° C.

4-Polyfluoroalkylaniline and 4-polyfluoroalkoxyaniline are commercially available or may be obtained by application or adaptation of the methods described in J. Org. Chem., 29, 1 (1964), and in patents U.S. Pat. No. 3,920,444, U.S. Pat. No. 2,436,100, DE 2,606,982, EP 205821 and EP 546391.

The derivatives of formula (II) for which $-R_3-R_4-R_5-R_6-$ represents a chain of formula $-CH_2-CH_2-CH_2-S-$, $-CH_2-CH_2-CH_2-Se-$, $-CH_2-CH_2-CH_2-O-$, $-CH_2-CH_2-CH_2-N(R_9)-$, $-CH_2-CH_2-S-CH_2-$, $-CH_2-C(alk)(alk')-S-CH_2-$, $-CH_2-CH(R_{10})-S-CH_2-$ in which $R_{10}$ represents an alkyl, $-CH_2-CH_2-Se-CH_2-$, $-CH_2-CH_2-O-CH_2-$ or $-CH_2-CH_2-N(R_9)-CH_2-$ radical may be obtained by reducing a derivative of formula:

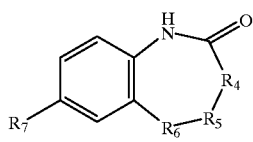

in which $R_7$ has the same meanings as in formula (I) and $—R_4—R_5—R_6—$ represents a chain of formula $—CH_2—CH_2—S—$, $—CH_2—CH_2—Se—$, $—CH_2—CH_2—O—$, $—CH_2—CH_2—N(R_9)—$, $—CH_2—S—CH_2—$, $—C(alk)(alk')—S—CH_2—$, $—CH(R_{10})—S—CH_2—$ in which $R_{10}$ represents an alkyl, $—CH_2—Se—CH_2—$, $—CH_2—O—CH_2—$ or $—CH_2—N(R_9)—CH_2—$ radical in which $R_9$ has the same meanings as in formula (I).

This reaction is generally carried out by means of a reducing agent such as lithium tetrahydroaluminate, in an inert organic solvent such as tetrahydrofuran, at a temperature close to 20° C. or the borane-dimethyl sulphide complex, in an inert solvent such as toluene, at the boiling point of the reaction medium.

The derivatives of formula (III) for which the chain $—R_4—R_5—R_6—$ represents a chain of formula $—CH_2—S—CH_2—$, $—C(alk)(alk')—S—CH_2—$, $—CH(R_{10})—S—CH_2—$ in which $R_{10}$ represents an alkyl or $—CH_2—Se—CH_2—$ radical may be obtained by cyclization of a derivative of formula:

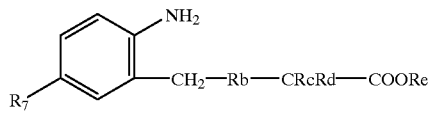

in which the amino functional group is optionally protected and either Rb represents a sulphur atom, Rc, Rd and Re each represent a hydrogen atom or an alkyl radical, and $R_7$ has the same meanings as in formula (I), or Rb represents a selenium atom, Rc and Rd each represent a hydrogen atom and Re represents an alkyl radical.

Preferably, the amino functional group is protected in the form of tert-butyl carbamate. When Re represents an alkyl radical, the cyclization is generally carried out by means of trifluoroacetic acid, in an inert organic solvent such as a chlorinated solvent (chloroform or dichlormethane for example) at a temperature close to 20° C. or alternatively by means of para-toluenesulphonic acid, in toluene, at the boiling point of the reaction medium. When Re represents a hydrogen atom, the cyclization is preferably carried out in xylene, by heating to the boiling point of the reaction medium.

The derivatives of formula (IV) for which Re represents an alkyl radical may be obtained by reacting sulphur or selenium, and then a derivative Hal—CRcRd—COOalk for which Hal represents a halogen atom, Rc and Rd have the same meanings as above, with the lithium derivative of a 2-methyl-4-polyfluoroalkylaniline or 2-methyl-4-polyfluoroalkoxyaniline whose amino functional group is protected, preferably in tert-butyl carbamate form, in tetrahydrofuran, at a temperature varying from about −70° C. to close to 20° C. The lithium derivative of 2-methyl-4-polyfluoroalky-laniline or 2-methyl-4-polyfluoroalkoxyaniline whose amino functional group is protected may be obtained by reacting tert-butyllithium with a 2-methyl-4-polyfluoroalkylaniline or 2-methyl-4-polyfluoroalkoxyaniline whose amino functional group is protected, in tetrahydrofuran, at a temperature of about −70° C. The derivatives of formula (IV) for which Re represents a hydrogen atom may be obtained by hydrolysing a corresponding derivative of formula (IV) for which Re represents an alkyl radical. This hydrolysis is generally carried out by means of sodium hydroxide, in ethanol, at a temperature between 15° C. and the boiling point of the reaction medium.

The 2-methyl-4-polyfluoroalkylaniline or 2-methyl-4-polyfluoroalkoxyaniline whose amino functional group is protected may be obtained by reacting iodomethane with the lithium derivative of a 4-polyfluoroalkylaniline or 4-polyfluoroalkoxyaniline whose amino functional group is protected, in tetrahydrofuran, at a temperature varying from about −70° C. to about 20° C.

The derivatives of formula (III) for which the chain $—R_4—R_5—R_6—$ represents a chain of formula $—CH_2—N(R_9)—CH_2—$ and the derivatives of formula (II) for which $—R_3—R_4—R_5—R_6—$ represents a chain $—CH_2—CO—N(R_9)—CH_2—$ may be obtained by reacting chloroacetyl chloride with an aniline of formula:

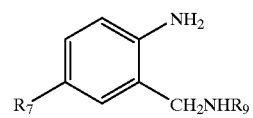

in which $R_7$ and $R_9$ have the same meanings as in formula (I), and separating the 2 derivatives.

This reaction is generally carried out in an inert organic solvent such as an ether (diethyl ether for example), in the presence of sodium hydrogen carbonate, at a temperature close to 20° C.

The anilines of formula (V) are obtained according to the following reaction scheme:

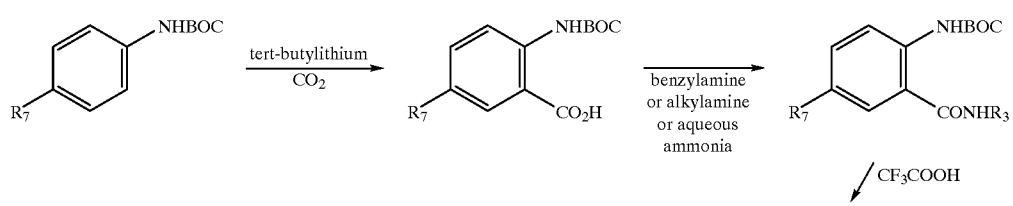

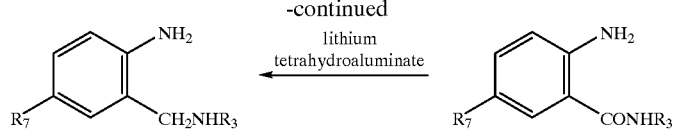

In these formulae, $R_7$ and $R_9$ have the same meanings as in formula (I) and BOC represents the tertbutoxycarbonyl radical. The operating conditions are defined in greater detail in Example 8.

The derivatives of formula (III) for which the chain —$R_4$—$R_5$—$R_6$— represents a chain —$CH_2$—O—$CH_2$— may be obtained by application or adaptation of the method described by E. TESTA and L. FONTANELLA, II Farmaco, 1965, 20, 323–335 according to the following reaction scheme:

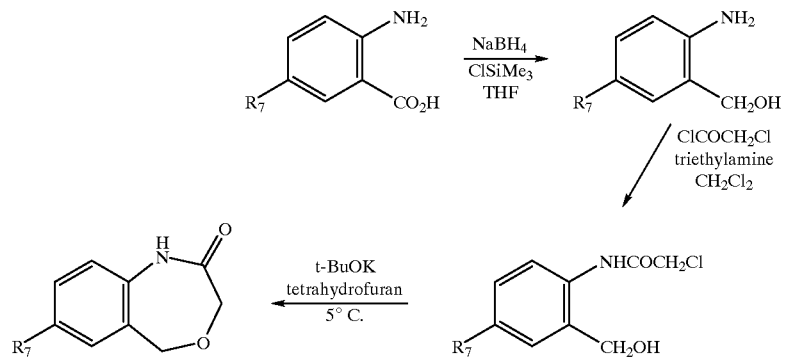

In these formulae, $R_7$ has the same meanings as in formula (I), Me represents a methyl radical and Bu represents a butyl radical.

The derivatives of formula (III) for which the chain —$R_4$—$R_5$—$R_6$— represents a chain of formula —$CH_2$—$CH_2$—S—, —$CH_2$—$CH_2$—Se—, —$CH_2$—$CH_2$—O—, —$CH_2$—$CH_2$—N($R_9$)— may be obtained from a derivative of formula:

(VI)

in which Rf represents an OH, SH, SeH or NH($R_9$) radical, $R_7$ and $R_9$ have the same meanings as in formula (I), by application or adaptation of the methods described in the examples and by X. HUANG, Synthesis, 851–852 (1984), W. C. LUMMA et al., J. Med. Chem., 24, 93–101 (1981) and E. J. JACOBSEN et al., J. Med. Chem., 39, 158–175 (1996).

The derivatives of formula (VI) may be obtained by application or adaptation of the methods described by R. BELCHER et al., J. Chem. Soc., 3846 (1954); B. L. MYLARY, J. Med. Chem., 34, 108–122 (1991); D. W. COMBS et al., J. Med. Chem., 35, 172–176 (1992), W. C. LUMMA et al., J. Med. Chem., 24, 93–101 (1981) and A. V. ZEIGER et al., J. Org. Chem., 42 (3), 542 (1977).

The derivatives of formula (II) for which —$R_3$—$R_4$—$R_5$—$R_6$— represents a radical —$CH_2$—$CH_2$—$CH_2$—OC— may be obtained by decarboxylation followed by deprotection of a derivative of formula:

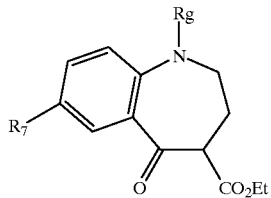

(VII)

in which $R_7$ has the same meanings as in formula (I), Rg represents a p-toluenesulphonyl radical and Et represents an ethyl radical.

This reaction is generally carried out by means of hydrochloric acid, in acetic acid, at the boiling point of the reaction medium. The deprotection is generally carried out by means of magnesium turnings, in a tetrahydrofuran and methanol mixture, at a temperature close to 20° C.

The derivatives of formula (VII) may be obtained according to the following reaction scheme:

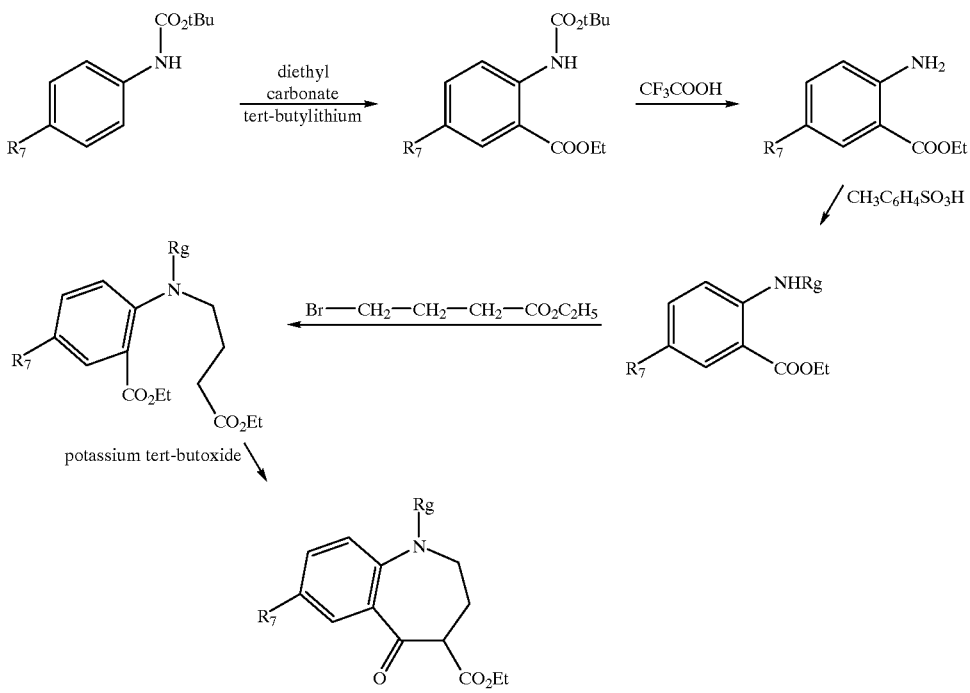

In these formulae, $R_7$ has the same meanings as in formula (I), Rg represents a p-toluenesulphonyl radical, Et represents an ethyl radical and tBu a tertbutyl radical. The operating conditions are defined in greater detail in Example 1.

The derivatives of formula (II) in which $-R_3-R_4-R_5-R_6-$ represents a radical $-CH_2-CH_2-CH_2-CH(R_8)-$ or $-CH_2-CH_2-CH(R_8)-CH_2-$ and $R_8$ represents a hydroxyl radical may be obtained by reducing a corresponding derivative of formula (II) for which $R_2$ represents a hydrogen atom or an alkyl radical and $-R_3-R_4-R_5-R_6-$ represents a chain of formula $-CH_2-CH_2-CO-CH_2-$ or $-CH_2-CH_2-CH_2-CO-$.

This reaction is carried out by any method which makes it possible to pass from a ketone to an alcohol. The procedure is generally carried out by means of sodium borohydride, in an alcohol such as methanol or ethanol, at a temperature of between 0 and 25° C.

The derivatives of formula (II) for which $-R_3-R_4-R_5-R_6-$ represents a radical $-CH_2-CH_2-CO-CH_2-$ may be obtained by decarboxylation-deprotection of a derivative of formula:

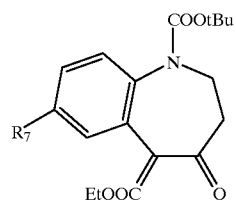

(VIII)

in which $R_7$ has the same meanings as in formula (I), tBu represents a tert-butyl radical and Et represents an ethyl radical.

This reaction is generally carried out by means of hydrochloric acid, in acetic acid, at the boiling point of the reaction medium.

The derivatives of formula (VIII) may be obtained according to the following reaction scheme:

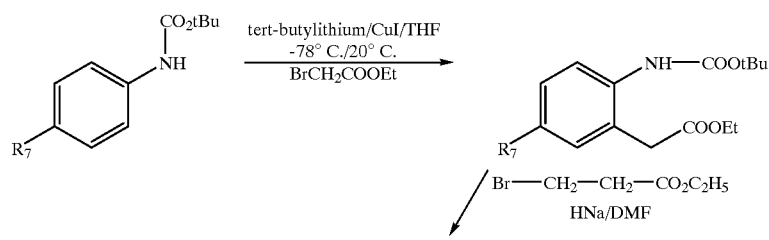

-continued

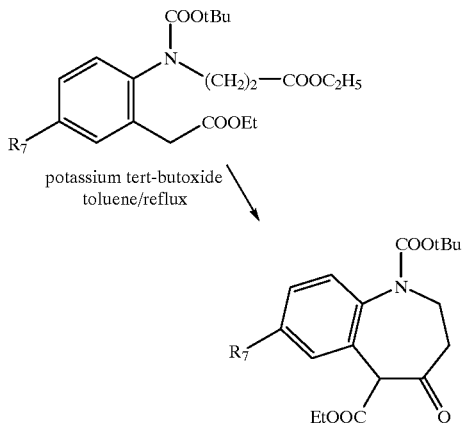

potassium tert-butoxide
toluene/reflux

In these formulae, $R_7$ has the same meanings as in Formula (I), Et represents an ethyl radical and tBu a tert-butyl radical.

The derivatives of formula (II) for which —$R_3$—$R_4$—$R_5$—$R_6$— represents a radical —$CH_2$—CH($R_{10}$)—S—$CH_2$— for which $R_{10}$ represents a —$CONH_2$ radical may be obtained by reacting ammonia with a corresponding derivative of formula (II) for which —$R_3$—$R_4$—$R_5$—$R_6$— represents a radical —$CH_2$—CH($R_{10}$)—S—$CH_2$— for which $R_{10}$ represents a COOalk radical.

This reaction is generally carried out in an inert solvent such as an alcohol (ethanol for example), at a temperature close to 20° C.

The derivatives of formula (II) for which —$R_3$—$R_4$—$R_5$—$R_6$— represents a radical —$CH_2$—CH($R_{10}$)—S—$CH_2$— for which $R_{10}$ represents a —COOalk radical may be obtained by reducing a derivative of formula:

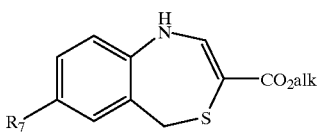

(IX)

in which $R_7$ has the same meanings as in formula (I).

This reaction is preferably carried out by means of magnesium, in an inert solvent such as an aliphatic alcohol (1–6C) (methanol for example), at a temperature of 40° C.

The derivatives of formula (IX) may be obtained according to the following reaction scheme:

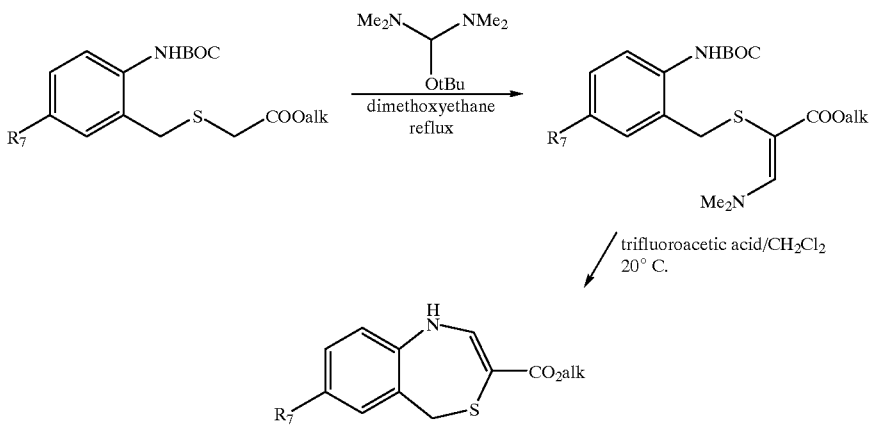

in these formulae, $R_7$ has the same meanings as in formula (I), alk represents an alkyl radical, BOC represents a tert-butoxycarbonyl radical.

It is understood for persons skilled in the art that, to carry out the processes according to the invention described above, it may be necessary to introduce groups for protecting amino functional groups so as to avoid side reactions. In particular, the procedure is carried out according to the methods described by T. W. Greene, Protective Groups in Organic Synthesis, A. Wiley Interscience Publication (1981), or by Mc Omie, Protective Groups in Organic Chemistry, Plenum Press (1973). The amino functional groups may, for example, be protected by methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl, acetyl or benzyloxycarbonyl radicals or their substituted derivatives or in the form of tert-butyl or methyl carbamates and then regenerated by means of trifluoroacetic acid or hydrochloric acid in tetrahydrofuran or of benzyl carbamates and then regenerated by hydrogenation after having used the process according to the invention.

The reaction mixtures obtained by the various procedures described above are treated according to conventional physical methods (evaporation, extraction, distillation, chromatography and crystallization for example) or conventional chemical methods (formation of salts for example).

The enantiomers of the compounds of formula (I) containing at least one asymmetric site may be obtained by synthesis from chiral precursors or by resolution of the racemates, for example, by chromato-graphy on a chiral stationary phase of the type comprising (S,S) WHELCK-01®, Chiralcel OJ® or a chiral column according to W. H. PIRKLE et al., asymmetric synthesis, vol 1, Academic Press (1983).

The compounds of formula (I) in the form of a free base may optionally be converted to addition salts with an inorganic or organic acid, by the action of such an acid in an organic solvent such as an alcohol, a ketone, an ether or a chlorinated solvent.

As examples of pharmaceutically acceptable salts, there may be mentioned the addition salts with inorganic or organic acids such as acetate, propionate, succinate, benzoate, fumarate, maleate, oxalate, methanesulphonate, isethionate, theophyllineacetate, salicylate, methylene-bis-β-oxynaphthoate, hydrochloride, sulphate, nitrate and phosphate.

The compounds of formula (I) exhibit advantageous pharmacological properties. These compounds are anticonvulsants and interfere with glutamatergic transmission and are therefore useful for the treatment or prevention of all ischaemias (such as flocal or global ischaemia) following cerebrovascular accidents such as thromboembolic and haemorrhagic stroke, cardiac arrest, arterial hypotension, cardiac, vascular or pulmonary surgery or severe hypoglycaemia. They are also useful in the treatment of the effects caused by anoxia, whether it is perinatal or subsequent to drowning, a high pressure or cerebrospinal lesions. These compounds may also be used to treat or prevent the development of neurodegenerative diseases, of HUNTINGDON's chorea, of ALZHEIMER's disease and other dementias, of amyotrophic lateral sclerosis or of other motor neuron diseases, of olivopontocerebellar atrophy and of PARKINSON's disease. These compounds may also be used against epileptogenic (epilepsy) and/or convulsive manifestations, for the treatment of cerebral or spinal traumas, of traumas linked to degeneration of the inner ear (R. PUJOL et al., Neuroreport, 3, 299–302 (1992)) or of the retina (J. L. MONSINGER et al., Exp. Neurol., 113, 10–17 (1991)), of tinnitus, of anxiety (KEHNE et al., Eur. J. Pharmacol., 193, 283 (1991)), of depression (TRULLAS et al., Eur. J. Pharmacol., 185, 1, (1990)), of schizophrenia (REYNOLDS, TIPS, 13, 116 (1992)), of TOURETTE's syndrome, of hepatic encephalopathies, of sleep disorders, of attention deficit disorders, of disorders of hormonal conditions (excess secretion of GH or LH, secretion of corticosterone), as analgesics (DICKENSON et al., Neurosc. Letters, 121, 263 (1991)), anti-inflammatory agents (SLUTA et al., Neurosc. Letters, 149, 99–102 (1993)), antianoretics (SORRELS et al., Brain Res., 572, 265 (1992)), antimigraine drugs, antiemetics and to treat poisoning by neurotoxins and other substances which are NMDA or AMPA receptor agonists, as well as neurological disorders associated with viral diseases such as viral meningitis and encephalitis, AIDS (LIPTON et al., Neuron 7, 111 (1991)), rabies, measles and tetanus (BAGETTA et al., Br. J. Pharmacol., 101, 776 (1990)). These compounds are also useful for the prevention of, tolerance to and dependency on the symptoms of withdrawal from drugs and alcohol, and of inhibition of addiction to and of dependency on opiates, barbiturates, amphetamine and benzodiazepines.

They may also be used in the treatment of deficiencies linked to mitochrondrial abnormalities such as mitochrondrial myopathy, LEBER's syndrome, WERNICKE's encephalopathy, RETT's syndrome, homocysteinaemia, hyperprolinaemia, hydroxybutyric-aminoaciduria, saturnine encephalopathy (chronic lead poisoning) and sulphite oxidase deficiency.

The activity of these compounds as anticonvulsant was determined in mice according to the maximum electroshock method. White CD1 mice are treated intravenously with the test compounds in saline medium 10 minutes before being subjected to an electric shock (75 mA; duration 0.04 second) by means of ocular electrodes. Normally, this shock produces a tonic convulsion in untreated mice, characterized by extension of the limbs. If tonic convulsion does not occur, the animal is considered to be protected. In this test, the compounds of formula (I) have an $ED_{50}$ of less than or equal to 4 mg/kg.

The activity of these compounds as antiglutamate was determined on the convulsions induced by glutamate according to a technique inspired by that of I. P. LAPIN, J. Neural. Transmission, 54, 229–238 (1982); the glutamate being injected by the intracerebroventricular route according to a technique inspired by that of R. CHERMAT and P. SIMON, J. Pharmacol. (Paris), 6, 489–492 (1975). Their $ED_{50}$ is less than 10 mg/kg.

The compounds of formula (I) have a low toxicity. Their $LD_{50}$ is greater than 15 mg/kg by the IV route in mice.

For medicinal use, the compounds of formula (I) may be used as such or in the form of pharmaceutically acceptable salts, that is to say which are nontoxic at the applicable doses.

Particularly advantageous are the compounds of formula (I) for which $R_7$ represents a trifluoromethoxy or trifluoromethyl radical.

The preferred compounds of formula (I) are those for which $R_1$ represents a sulphur atom, $R_2$ represents a hydrogen atom, —$R_3$—$R_4$—$R_5$—$R_6$— represents a chain of formula —$CH_2$—$CH_2$—$CH_2$—$CH_2$—, —$CH_2$—$CH_2$—$CH_2$—CO—, —$CH_2$—$CH_2$—$CH_2$—$CH(R_8)$—, —$CH_2$—$CH_2$—$CH_2$—Se—, —$CH_2$—$CH_2$—Se—$CH_2$—, —$CH_2$—$CH_2$—$CH_2$—S—, —$CH_2$—$CH_2$—$CH_2$—SO—, —$CH_2$—$CH_2$—$CH_2$—$SO_2$—, —$CH_2$—$CH_2$—$CH_2$—O—, —$CH_2$—$CH_2$—$CH_2$—$N(R_9)$—, —$CH_2$—$CH_2$—CO—$CH_2$—, —$CH_2$—$CH_2$—$CH(R_8)$—$CH_2$—, —$CH_2$—$CH_2$—S—$CH_2$—, —$CH_2$—$CH_2$—SO—$CH_2$—, —$CH_2$—$CH_2$—$SO_2$—$CH_2$—, —$CH_2$—C(alk) (alk')—S—$CH_2$—$CH_2$—$CH(R_{10})$—S—$CH_2$—, —$CH_2$—$CH_2$—O—$CH_2$—, —$CH_2$—$CH_2$—$N(R_9)$—$CH_2$— or —$CH_2$—CO—$N(R_9)$—$CH_2$—, $R_7$ represents a trifluoromethyl or trifluoromethoxy radical, $R_8$ represents a hydroxyl radical, $R_9$ represents a hydrogen atom or an alkyl or benzyl radical, $R_{10}$ represents an alkyl, —$CH_2OH$, —COOalk, —COOH or —$CONH_2$ radical, alk represents an alkyl radical and alk' represents an alkyl radical, their isomers, racemates, enantiomers and their salts.

More particularly advantageous are the following compounds of formula (I):

2-imino-9-trifluoromethoxy-4,5,6,7-tetrahydro-2H-thiazolo[5,4,3-jk][1]benzazepin-7-ol, 2-imino-9-trifluoromethoxy-4,5,6,7-tetrahydro-2H-thiazolo[5,4,3-jk][1]benzazepine, 2-imino-9-trifluoromethyl-4,5,6,7-tetrahydro-2H-thiazolo[5,4,3-jk][1]benzazepine, 2-imino-9-trifluoromethoxy-5,6-dihydro-2H,4H-thiazolo[3,4,5-ef][1,5]benzothiazepine 7,7-dioxide, 2-imino-9-trifluoromethoxy-5,6-dihydro-2H,4H-thiazolo [3,4,5-ef][1,5]benzothiazepine 7-oxide, 2-imino-9-trifluoromethoxy-5,6-dihydro-2H,4H-thiazolo [3,4,5-ef][1,5]benzothiazepine, 6-benzyl-2-imino-9-trifluoromethoxy-6,7-dihydro-4H- thiazolo[3,4,5-kj][1,4]benzodiazepin-5-one, 6-benzyl-2-imino-9-trifluoromethoxy-4,5,6,7-tetrahydro- 2H-thiazolo[3,4,5-kj][1,4]benzodiazepine, 2-imino-9-trifluoromethoxy-4,5-dihydro-2H,7H-thiazolo [3,4,5-de][4,1]benzothiazepine, 2-imino-9-trifluoromethyl-4,5-dihydro-2H,7H-thiazolo [3,4,5-de][4,1]benzothiazepine, 2-imino-9-trifluoromethyl-4,5-dihydro-2H,7H-thiazolo [3,4,5-de][4,1]benzothiazepine 6,6-dioxide, 2-imino-9-trifluoromethyl-5,6-dihydro-2H,4H-thiazolo [3,4,5-ef][1,5]benzothiazepine 7-oxide, 2-imino-9-trifluoromethyl-5,6-dihydro-2H,4H-thiazolo [3,4,5-ef][1,5]benzothiazepine 6,6-dioxide, 2-imino-9-trifluoromethyl-5,6-dihydro-2H,4H- thiazolo[3,4,5-ef][1,5]benzothiazepine, 2-imino-9-trifluoromethyl-4,5,6,7-tetrahydro-2H- thiazolo[5,4,3-jk][1]benzazepin-7-ol, 2-imino-9-trifluoromethoxy-4,5-dihydro-2H,7H-thiazolo [3,4,5-de][4,1]benzothiazepine 6,6-dioxide, 2-imino-9-trifluoromethoxy-4,5-dihydro-2H,7H-thiazolo [3,4,5-de][4,1]benzothiazepine 6-oxide, 6-benzyl-2-imino-9-trifluoromethyl-6,7-dihydro-4H- thiazolo[3,4,5-jk][1,4]benzodiazepin-5-one, 6-benzyl-2-imino-9-trifluoromethyl-4,5,6,7-tetrahydro- 2H-thiazolo[3,4,5-jk][1,4]benzodiazepine, 2-imino-5-methyl-9-trifluoromethyl-4,5-dihydro-2H,7H- thiazolo[3,4,5-de][4,1]benzothiazepine, 5-carbamoyl-2-imino-9-trifluoromethyl-4,5-dihydro-2H, 7H-thiazolo[3,4,5-de][4,1]benzothiazepine, 5,5-dimethyl-2-imino-9-trifluoromethyl-2H,4H,7H- thiazolo[3,4,5-de][4,1]benzothiazepine, 5-hydroxymethyl-2-imino-9-trifluoromethyl-4,5- dihydro-2H,7H-thiazolo[3,4,5-de][4,1] benzothiazepine, their isomers, racemates, enantiomers and their salts.

Particularly preferred are the following compounds:

(R,S)-2-imino-9-trifluoromethyl-4,5-dihydro-2H,7H- thiazolo[3,4,5-de][4,1]benzothiazepine 6-oxide, (+)-2-imino-9-trifluoromethyl-4,5-dihydro-2H,7H- thiazolo[3,4,5-de][4,1]benzothiazepine 6-oxide, (−)-2-imino-9-trifluoromethyl-4,5-dihydro-2H,7H- thiazolo[3,4,5-de][4,1]benzothiazepine 6-oxide, (R,S)-2-imino-5-methyl-9-trifluoromethyl-4,5-dihydro- 2H,7H-thiazolo[3,4,5-de][4,1]benzothiazepine, (+)-2-imino-5-methyl-9-trifluoromethyl-4,5-25 dihydro- 2H,7H-thiazolo[3,4,5-de][4,1]benzothiazepine, (−)-2-imino-5-methyl-9-trifluoromethyl-4,5-dihydro-2H, 7H-thiazolo[3,4,5-de][4,1]benzothiazepine and their salts.

The following examples illustrate the invention without limiting it.

EXAMPLE 1

1.2 g of bromine diluted in 10 ml of acetic acid are added dropwise over 10 minutes, at a temperature close to 20° C., to a solution of 1.7 g of potassium thiocyanate and 1.9 g of (R,S)-7-trifluoromethoxy-2,3,4,5-tetrahydro-1H-[1] benzazepin-5-ol in 30 ml of acetic acid. The reaction mixture is stirred for 20 hours at the same temperature, poured over ice, alkalinized with a solution of aqueous ammonia at 20% and extracted with three times 100 ml of ethyl acetate. The organic phases are combined, washed with 100 ml of distilled water, dried over magnesium sulphate and concentrated to dryness under reduced pressure (2 kPa) at 40° C. The residue (0.4 g) is chromatographed on a silica gel, eluting with ethyl acetate. The product isolated is taken up in a mixture of 4 ml of isopropyl ether and petroleum ether (50-50 by volume) and 0.15 g of (R,S)-2-imino-9- trifluoromethoxy-4,5,6,7-tetrahydro-2H-thiazolo[5,4,3-jk] [1]benzazepin-7-ol is thus obtained in the form of a cream-coloured solid melting at 167° C. [analysis $C_{12}H_{11}F_3N_2O_2S$, % calculated C: 47.37, H: 3.64, F: 18.73, N: 9.21, O: 10.52, S: 10.54, % found C: 47.6, H: 3.5, F: 18.4, N: 9.1, S: 10.6].

(R,S)-7-Trifluoromethoxy-2,3,4,5-tetrahydro-1H-[1] benzazepin-5-ol may be prepared in the following manner: 1.08 g of magnesium turnings are added at a temperature close to 20° C. to a solution of 3.6 g of (R,S)-1-(4- toluenesulphonyl)-7-trifluoromethoxy-2,3,4,5-tetrahydro- 1H-[1]benzazepin-5-ol in 30 ml of tetrahydrofuran and 40 ml of methanol. The reaction mixture is stirred for 24 hours at the same temperature, poured into distilled water and the gelatinous mass formed, taken up in ethyl ether, is filtered and then washed three times with 40 ml of ethyl ether. The pale yellow filtrate thus obtained is dried over magnesium sulphate and then evaporated under reduced pressure at 50° C. 1.9 g of (R,S)-7-trifluoro-methoxy-2,3,4,5-tetrahydro- 1H-[1]benzazepin-5-ol are thus obtained in the form of a cream-coloured solid melting at 110° C.

(R,S)-1-(4-Toluenesulphonyl)-7-trifluoro-methoxy-2,3,4, 5-tetrahydro-1H-[1]benzazepin-5-ol may be prepared in the following manner: 0.7 g of sodium borohydride is added in small portions to a solution of 3.7 g of 1-(4- toluenesulphonyl)-7-trifluoromethoxy-2,3-dihydro-1H,4H- [1]benzazepin-5-one in 40 ml of ethanol and the mixture is kept stirred for 2 hours at a temperature close to 20° C. After the usual treatment, 3 g of (R,S)-1-(4-toluenesulphonyl)-7- trifluoromethoxy-2,3,4,5-tetrahydro-1H-[1]benzazepin-5-ol are obtained in the form of a beige solid melting at 160° C.

1-(4-Toluenesulphonyl)-7-trifluoromethoxy-2,3-dihydro- 1H,4H-[1]benzazepin-5-one may be prepared in the following manner: 5 ml of hydrochloric acid are added to a solution of 2.2 g of ethyl 5-oxo-1-(4-toluenesulphonyl)-7- trifluoromethoxy-2,3,4,5-tetrahydro-1H-[1]benzazepine-4- carboxylate in 20 ml of acetic acid. The formation of a white precipitate is observed and the reaction mixture is kept under reflux for 4 hours. It is concentrated to dryness under reduced pressure, the yellow oil obtained is taken up in 300 ml of ethyl ether and the mixture is washed with a saturated sodium hydrogen carbonate solution. After decantation, washing twice with 50 ml of distilled water and with a saturated sodium chloride solution, the organic phase is dried over magnesium sulphate, filtered and concentrated to dryness under reduced pressure (2.2 kPa) at 60° C. 1.58 g of 1-(4-toluenesulphonyl)-7-trifluoromethoxy-2,3-dihydro- 1H,4H-[1]benzazepin-5-one are thus obtained in the form of a beige solid melting at 96° C.

Ethyl 5-oxo-1-(4-toluenesulphonyl)-7-trifluoromethoxy- 2,3,4,5-tetrahydro-1H-[1]benzazepine-4-carboxylate may be prepared in the following manner: 9.97 g of potassium tert-butoxide are added to 275 ml of anhydrous toluene heated to reflux temperature, under an argon atmosphere, and then a solution of 23 g of ethyl 2-[(3- ethoxycarbonylpropyl)-(4-toluenesulphonyl)amino]-5- trifluoromethoxybenzoate in 300 ml of anhydrous toluene is introduced dropwise. Once the addition is complete, the heating is continued for one hour. After cooling, 90 ml of a 1 N solution of hydrochloric acid are added, the mixture is taken up in distilled water and after decantation, the organic phase is washed with a saturated sodium chloride solution, dried over magnesium sulphate, filtered and concentrated to dryness under reduced pressure (2.2 kPa) at 60° C. The residue obtained is dissolved in 100 ml of boiling cyclohexane and after cooling, the precipitate appearing is separated by filtration and dried at 40° C. under reduced pressure (70 Pa). 10.75 g of ethyl 5-oxo-1-(4-toluenesulphonyl)-7-trifluoromethoxy-2,3,4,5-tetrahydro-1H-[1]benzazepine-4-carboxylate are thus obtained in the form of a beige powder melting at 97° C.

Ethyl 2-[(3-ethoxycarbonylpropyl)-(4-toluenesulphonyl) amino]-5-trifluoromethoxybenzoate may be prepared in the following manner: a mixture of 5.5 g of ethyl 2-(4-toluenesulphonyl)amino-5-trifluoromethoxybenzoate, 5.6 g of potassium carbonate, 3.18 g of ethyl 4-bromobutyrate in 30 ml of dimethylformamide. The mixture is concentrated to dryness under reduced pressure (2.2 kPa) at 60° C. The brown oil obtained is dissolved in ethyl acetate and the solution is washed with distilled water and then with a saturated sodium chloride solution, dried over magnesium sulphate and then concentrated to dryness under reduced pressure (2.2 kPa) at 50° C. 5.7 g of ethyl 2-[(3-ethoxycarbonylpropyl)-(4-toluenesulphonyl)amino]-5-trifluoromethoxy-benzoate are thus obtained in the form of a yellow oil [$^1$H NMR spectrum in DMSO-$d_6$, T=300K, δ in ppm (300 Mhz) 1.10 (3H, t, J=6 Hz, $CH_3$) , 1.30 (3H, t, J=6 Hz, $CH_3$) , 1.65 (2H, m, $CH_2$), 2.40 (5H, m, $COCH_2$ and $PhCH_3$), 3.45 and 3.70 (1H each, m, $NCH_2$), 4.00 (2H, q, J=6 Hz, $OCH_2$), 4.25 (2H, q, J=6 Hz, $OCH_2$), 7.05 (1H, d, J=8 Hz, arom. CH), 7.40 (4H, s, 4 tosyl CH), 7.65 (1H, dd, J=8 and 2 Hz, arom. CH), 7.70 (1H, d, J=2 Hz, arom. CH)].

Ethyl 2-(4-toluenesulphonyl)amino-5-trifluoromethoxybenzoate may be prepared in the following manner: 16.1 g of 4-toluenesulphonyl chloride are added, with stirring and at a temperature close to 20° C. to a solution of 17.5 g of ethyl 2-amino-5-trifluoromethoxybenzoate in 70 ml of pyridine. After stirring for 24 hours, the mixture is concentrated to dryness under reduced pressure (2.2 kPa) at 60° C. The brown oil obtained is dissolved in ethyl acetate and the solution is washed successively with a hydrochloric acid solution (2 N) with distilled water and with a saturated sodium chloride solution, and then dried over magnesium sulphate and concentrated to dryness under reduced pressure (2.2 kPa) at 50° C. The orange-coloured oil obtained, taken up in petroleum ether, gives 27.8 g of ethyl 2-(4-toluenesulphonyl) amino-5-trifluoromethoxybenzoate in the form of a white powder melting at 76° C.

Ethyl 2-amino-5-trifluoromethoxybenzoate may be prepared in the following manner: 55 ml of trifluoroacetic acid are added to 21 g of ethyl 2-tertbutoxycarbonylamino-5-trifluoromethoxybenzoate in 150 ml of dichloromethane. After 4 hours at a temperature close to 20° C., the black solution obtained is concentrated to dryness. The residue is treated with a dilute sodium hydrogen carbonate solution and extracted with petroleum ether. The organic phase is washed with distilled water until a neutral pH is obtained, dried over magnesium sulphate and concentrated to dryness under reduced pressure (2.2 kPa) at 50° C. 14 g of ethyl 2-amino-5-trifluoromethoxybenzoate are thus obtained in the form of a brown oil [$^1$H NMR spectrum in DMSO-$d_6$, T=300K, δ in ppm (300 Mhz): 1.30 (3H, t, J=6 Hz, $CH_3$), 4.30 (2H, q, J=6 Hz, $OCH_2$), 6.85 (2H, s, $NH_2$), 6.87 (1H, d, J=8 Hz, arom. CH), 7.30 (1H, dd, J=8 and 2 Hz, arom. CH), 7.55 (1H, d, J=2 Hz, arom. CH)].

Ethyl 2-tert-butoxycarbonylamino-5-trifluoromethoxybenzoate may be prepared in the following manner: 200 ml of a 1.5 M solution of tert-butyllithium in pentane are poured, over 1 hour, over a solution of 34.5 g of tert-butyl 4-trifluoromethoxyphenylcarbamate in 430 ml of anhydrous tetrahydrofuran, maintained under argon at −78° C. The temperature is allowed to rise to about −20° C. and the mixture is kept stirred for 2.5 hours. The reaction medium is again cooled to around −78° C. and 75 ml of diethyl carbonate are poured all at once. After 16 hours at a temperature close to 20° C., 100 ml of a saturated aqueous ammonium chloride solution and 250 ml of ethyl ether are added. After decantation, the aqueous phase is again extracted with twice 200 ml of ethyl ether. The organic extracts are combined, washed with distilled water and with a saturated aqueous sodium chloride solution, dried over magnesium sulphate and concentrated to dryness under reduced pressure. The red oil obtained is dissolved in petroleum ether and the solution is filtered on a silica gel, washing with petroleum ether. The filtrate, concentrated to dryness, gives a red oil which crystallizes. After recrystallization from 50 ml of hexane, 21.5 g of ethyl 2-tert-butoxycarbonylamino-5-trifluoromethoxybenzoate are obtained in the form of a cream-coloured solid melting at 82° C.

tert-Butyl 4-trifluoromethoxyphenylcarbamate may be prepared in the following manner: a solution of 47 g of di-tert-butyl dicarbonate in 100 ml of anhydrous tetrahydrofuran is poured, over 10 minutes and at 0° C., over a solution of 32.75 g of 4-trifluoromethoxyaniline in 150 ml of anhydrous tetrahydrofuran. The reaction medium is stirred at 80° C. for 3 hours, and then concentrated to dryness. A white crystallized product is obtained which is redissolved in 300 ml of ethyl acetate. The solution is washed three times with distilled water, dried over magnesium sulphate and concentrated to dryness. By trituration in petroleum ether, filtration and drying under reduced pressure (70 Pa) at 20° C., 35.5 g of tert-butyl 4-trifluoromethoxyphenylcarbamate are obtained in the form of a white solid melting at 110° C.

EXAMPLE 2

The procedure is carried out as in Example 1, but starting with 0.7 g of bromine in 5 ml of acetic acid, 1 g of 7-trifluoromethoxy-2,3,4,5-tetrahydro-1H-[1]benzazepine and 1.46 g of potassium thiocyanate in 15 ml of acetic acid. The thick orange-coloured oil isolated is chromatographed on a silica gel, eluting with a mixture of ethyl acetate and petroleum ether (70-30 by volume). A yellow oil is obtained which is dissolved in isopropyl ether to which there is added 0.45 ml of a hydrochloric isopropanol solution (about 5 N). The white precipitate formed is filtered and then dried under vacuum (70 Pa) at a temperature of 40° C. 0.52 g of 2-imino-9-trifluoromethoxy-4,5,6,7-tetrahydro-2H-thiazolo [5,4,3-jk][1]benzazepine hydrochloride is thus obtained in the form of a white solid melting at 270° C. (with decomposition) [analysis $C_{12}H_{12}ClF_3N_2OS$, % calculated C: 44.38, H: 3.72, Cl: 10.92, F: 17.55, N: 8.63, O: 4.93, S: 9.87, % found C: 44.3, H: 3.5, Cl: 10.9, F: 17.7, N: 9.1].

7-Trifluoromethoxy-2,3,4,5-tetrahydro-1H-[1] benzazepine may be prepared in the following manner: 5 ml of trifluoroacetic acid are added to a solution of 2.3 g of tert-butyl 7-trifluoromethoxy-2,3,4,5-tetrahydro-1H-[1] benzazepine-1-carboxylate in 25 ml of dichloromethane. After 1 hour at a temperature close to 20° C., the red solution obtained is concentrated to dryness under reduced pressure. The residue is treated with a dilute sodium hydrogen carbonate solution and extracted with ethyl ether. The organic phase is washed with distilled water and then with a saturated sodium chloride solution, dried over magnesium sulphate and concentrated to dryness under reduced pressure (2.2 kPa) at 50° C. 1.3 g of a brown oil are thus obtained, which oil is chromatographed on a silica gel, eluted with a mixture of petroleum ether and dichloromethane (70-30 by volume). After evaporation under reduced pressure, 1.14 g of 7-trifluoromethoxy-2,3,4,5-tetrahydro-1H-[1] benzazepine are isolated in the form of a pasty solid which is used as such in the next step [$^1$H NMR spectrum in DMSO-d$_6$, T=300K, δ in ppm (300 Mhz): between 1.50 and 1.70 (4H, m, 2 CH$_2$) , 2.60 (2H, m, PhCH$_2$), 2.90 (2H, m, NCH$_2$), 5.40 (1H, s, NH), between 6.80 and 7.00 (3H, m, 3 arom. CH)].

Tert-butyl 7-trifluoromethoxy-2,3,4,5-tetrahydro-1H-[1] benzazepine-1-carboxylate may be prepared in the following manner: 32 ml of a 1.5 M solution of tert-butyllithium in pentane are added over 1 hour to a solution, kept under an argon atmosphere at −78° C., of 5.54 g of tert-butyl 4-trifluoromethoxyphenylcarbamate in 60 ml of anhydrous tetrahydrofuran. The reaction mixture is then stirred for 2.5 hours at a temperature close to −20° C. It is again cooled to around −78° C. and 2.65 ml of 1-chloro-4-iodobutane are poured in dropwise over 15 minutes. The reaction mixture is heated to and kept at boiling temperature for 5 hours. After cooling, 50 ml of a saturated aqueous ammonium chloride solution are added and the mixture is extracted three times with a total of 200 ml of ethyl ether. The organic extracts are combined, washed with distilled water and with a saturated aqueous sodium chloride solution, dried over magnesium sulphate and then concentrated to dryness under reduced pressure. The oil obtained (6.65 g) is chromatographed on a silica gel, eluting with a mixture of petroleum ether and dichloromethane (50-50 by volume). 2.3 g of tert-butyl 7-trifluoromethoxy-2,3,4,5-tetrahydro-1H-[1]benzazepine-1-carboxylate are thus obtained in the form of a yellow oil [$^1$H NMR spectrum in DMSO-d$_6$, T=393K, δ in ppm (200 Mhz): between 1.65 and 1.90 (4H, m, 2 CH$_2$), 2.70 (2H, m, PhCH$_2$), 3.50 (2H, t, J=6 Hz, NCH$_2$), between 7.05 and 7.35 (3H, m, 3 arom. CH)].

EXAMPLE 3

The procedure is carried out as in Example 1, but starting with 2.38 g of bromine in 5 ml of acetic acid, 3.2 g of 7-trifluoromethyl-2,3,4,5-tetrahydro-1H-[1]benzazepine and 5 g of potassium thiocyanate in 35 ml of acetic acid. The brown-yellow oil isolated is chromatographed on a silica gel, eluting with ethyl acetate. A yellow oil is obtained which is dissolved in 15 ml of isopropyl ether to which there is added 1 ml of a 1.94 N solution of methanesulphonic acid in isopropanol. The white precipitate formed is filtered off and then dried under vacuum (70 Pa) at 50° C. 0.7 g of 2-imino-9-trifluoromethyl-4,5,6,7-tetrahydro-2H-thiazolo [5,4,3-jk][1]benzazepine methanesulphonate is thus obtained in the form of a white solid melting at 226° C. [analysis C$_{13}$H$_{15}$F$_3$N$_2$O$_3$S, % calculated C 42.38, H: 4.1, F: 15.2, N: 7.5, O: 13.3, S: 17.41, % found C: 42.4, H: 3.9, F: 15.2, N: 7.5, S: 17.4].

7-Trifluoromethyl-2,3,4,5-tetrahydro-1H-[1]benzazepine may be prepared as in Example 2, but starting with 5 g of tert-butyl 7-trifluoromethyl-2,3,4,5-tetrahydro-1H-[1] benzazepine-1-carboxylate in 50 ml of dichloromethane and 5 ml of trifluoroacetic acid. 3.3 g of 7-trifluoromethyl-2,3, 4,5-tetrahydro-1H-[[1]benzazepine are thus obtained in the form of a red oil which is used as such in the next step [$^1$H NMR spectrum in DMSO-d$_6$, T=300K, δ in ppm (300 Mhz): between 1.60 and 1.90 (4H, m, 2 CH$_2$), 2.75 (2H, t, J=6 Hz, PhCH$_2$), 3.00 (2H, t, J=6 Hz, NCH$_2$), 5.90 (1H, broad s, NH), 6.90 (1H, d, J=8 Hz, arom. CH), 7.28 (1H, dd, J=2 and 8 Hz, arom. CH), 7.33 (1H, d, J=2Hz, arom. CH)].

Tert-butyl 7-trifluoromethyl-2,3,4,5-tetrahydro-1H-[1] benzazepine-1-carboxylate may be prepared as in Example 2, but starting with 26.1 g of tert-butyl 4-trifluoromethylphenylcarbamate in 300 ml of anhydrous tetrahydrofuran, 160 ml of a 1.5 M solution of tert-butyllithium and 24 g of 1-chloro-4-iodobutane. 36 g of a brown oil are obtained, which oil is chromatographed on a silica gel, eluted with a mixture of petroleum ether and dichloromethane (70-30 by volume). 16.2 g of tert-butyl 7-trifluoromethyl-2,3,4,5-tetrahydro-1H-[1]benzazepine-1-carboxylate are thus obtained in the form of a greenish oil which is used as such in the next step.

EXAMPLE 4

A solution of 1.55 g of 3-chloroperbenzoic acid (80% purity) in 10 ml of dichloromethane is added dropwise over 15 minutes and at a temperature close to 20° C. to a solution of 1 g of 2-imino-9-trifluoromethoxy-5,6-dihydro-2H,4H-thiazolo[3,4,5-ef][1,5]benzothiazepine in 20 ml of dichloromethane, and the mixture is then stirred for 24 hours at the same temperature. 100 ml of a 1 M aqueous sodium hydrogen carbonate solution are then added and the mixture is stirred for 1 hour at the same temperature. After separation of the two phases, the aqueous phase is extracted twice with 50 ml of dichloromethane and the combined organic extracts are dried over magnesium sulphate and concentrated to dryness under reduced pressure (2 kPa). The product obtained (1.4 g) is chromatographed under nitrogen pressure (150 kPa) on 30 g of 20–45 μm silica gel contained in a column 2 cm in diameter, eluting with ethyl acetate. The product obtained (300 mg) is dissolved in 35 ml of absolute ethanol, to which 69 ml of methanesulphonic acid are added. After stirring for 1 hour at a temperature close to 20° C., the solution is concentrated to dryness under reduced pressure (2 kPa). The product obtained is suspended in isopropanol, separated by filtration, washed with isopropanol and isopropyl ether and dried under reduced pressure. 0.21 g of 2-imino-9-trifluoromethoxy-5,6-dihydro-2H,4H-thiazolo[3, 4,5-ef][1,5]benzothiazepine 7,7-dioxide methanesulphonate is thus obtained in the form of a white solid melting at a temperature greater than 260° C. [analysis C$_{12}$H$_{13}$F$_3$N$_2$O$_6$S$_3$, % calculated C: 33.17, H: 3.02, F: 13.12, N: 6.45, O: 22.10, S: 22.14, % found C: 33.20, H: 2.71, F: 12.7, N: 6.30, S: 22.1].

EXAMPLE 5

A solution of 770 mg of 3-chloroperbenzoic acid (80% purity) in 5 ml of dichloromethane is added dropwise over 15 minutes and at a temperature close to 0° C. to a solution of 1 g of 2-imino-9-trifluoromethoxy-5,6-dihydro-2H,4H-thiazolo[3,4,5-ef][1,5]benzothiazepine in 30 ml of dichloromethane, and the mixture is then stirred for 1 hour at the same temperature. 35 ml of a 1 M aqueous sodium hydrogen carbonate solution are then added and the mixture is stirred for 1 hour at 20° C. After separation of the two phases, the aqueous phase is extracted with 15 ml of dichloromethane and the combined organic extracts are dried over magnesium sulphate and concentrated to dryness under reduced pressure (2 kPa). The product obtained is suspended in 20 ml of isopropyl ether, separated by filtration, washed with isopropyl ether and dried under reduced pressure. The product obtained (716 mg) is dissolved in 70 ml of absolute ethanol and the solution is filtered and then supplemented with 160 ml of methanesulphonic acid. After stirring for 1 hour at a temperature close to 20° C., the solution is concentrated to dryness under reduced pressure (2 kPa). The product obtained is suspended in isopropanol, separated by filtration, washed with isopropanol and isopropyl ether and dried under reduced pressure. 0.70 g of 2-imino-9-trifluoromethoxy-5,6-dihydro-2H,4H-thiazolo[3,4,5-ef][1,5]benzothiazepine 7-oxide methanesulphonate is thus obtained in the form of a cream-coloured solid melting at a temperature greater than 260° C. [analysis $C_{12}H_{13}F_3N_2O_5S_3$, % calculated C: 34.45, H: 3.13, F: 13.62, N: 6.69, O: 19.12, S: 22.99, % found C: 34.44, H: 2.86, F: 13.37, N: 6.68, S: 22.8].

EXAMPLE 6

The procedure is carried out as in Example 1, but starting with 0.4 ml of bromine in 5 ml of acetic acid, 2 g of 8-trifluoromethoxy-2,3,4,5-tetrahydro-[1,5]benzothiazepine and 1.71 g of potassium thiocyanate in 24 ml of acetic acid. The crude product obtained is chromatographed under nitrogen pressure (150 kPa) on 40 g of 20–45 μm silica gel contained in a column 2.5 cm in diameter, eluting with a mixture of ethyl acetate and cyclohexane (50-50 by volume). 0.5 g of the product obtained (out of 1.5 g obtained in total) is dissolved in 80 ml of ethanol to which 0.117 ml of methanesulphonic acid is added. After stirring for 16 hours at 20° C., the solution is concentrated to dryness under reduced pressure (2 kPa). The product obtained is suspended in 20 ml of isopropyl ether, separated by filtration, washed with isopropyl ether and dried under reduced pressure (2 kPa) at 20° C. 0.56 g of 2-imino-9-trifluoromethoxy-5,6-dihydro-2H,4H-thiazolo[3,4,5-ef][1,5]benzothiazepine methanesulphonate is thus obtained in the form of a beige solid melting at a temperature greater than 260° C. [analysis $C_{12}H_{13}F_3N_2O_4S_3$, % calculated C: 35.82, H: 3.26, F: 14.16, N: 6.96, O: 15.9, S: 23.9, % found C: 35.8, H: 3.0, F: 14.3, N: 7.00, S: 23.8].

8-Trifluoromethoxy-2,3,4,5-tetrahydro-[1,5]-enzothiazepine may be prepared in the following manner: a solution of 2.5 g of 8-trifluoromethoxy-2,3-dihydro-5H-[1,5]benzothiazepin-4-one in 25 ml of tetrahydrofuran is added dropwise over 15 minutes to 21.4 ml of an approximately 0.5 M solution of lithium tetrahydroaluminate in tetrahydrofuran, kept under argon at 5° C. The reaction mixture is then stirred for 2 hours at 20° C. and 500 ml of distilled water, 100 ml of ethyl acetate and 100 ml of a saturated sodium chloride solution are added successively. After decantation, the aqueous phase is extracted three times with 50 ml of ethyl acetate. The organic extracts are combined, dried over magnesium sulphate and concentrated to dryness under reduced pressure (2 kPa). 2 g of 8-trifluoromethoxy-2,3,4,5-tetrahydro-[1,5]benzothiazepine are thus obtained in the form of a yellow oil [$^1$H NMR spectrum in DMSO-$d_6$, T=300K, δin ppm (300 Mhz): 1.95 (2H, m, CH$_2$); 3.00 (2H, m, SCH$_2$); 3.30 (2H, m, NCH$_2$); 5.90 (1H, m, NH); 6.85 (1H, d, J=8 Hz, arom. CH); 7.00 (1H, d, J=8Hz, arom. CH); 7.12 (1H, s, arom. CH)].

8-Trifluoromethoxy-2,3-dihydro-5H-[1,5]benzothiazepin-4-one may be prepared in the following manner: 70 g of potassium hydroxide pellets are added in portions of about 10 g to a suspension of 11.5 g of 2-amino-6-trifluoromethoxybenzothiazole in 115 ml of distilled water. The mixture is then stirred for 16 hours under reflux. After cooling to about 20° C., 16.4 g of ethyl 3-bromopropionate are added followed by 30 ml of distilled water, and the medium is stirred for 16 hours at the same temperature. The mixture is then acidified with concentrated hydrochloric acid at a temperature close to 5° C., and extracted three times with 50 ml of ethyl acetate. The organic extracts are combined, washed 3 times with distilled water, dried over magnesium sulphate and concentrated to dryness under reduced pressure (2 kPa). The crude product obtained is chromatographed under nitrogen pressure (150 kPa) on 250 g of 20–45 μm silica gel contained in a column 4 cm in diameter, eluting with a mixture of ethyl acetate and cyclohexane (75-25 by volume). 2.5 g of a white solid are thus obtained, which solid is resuspended in isopropyl ether, separated by filtration, washed with isopropyl ether and dried under reduced pressure (2 kPa). 1.6 g of 8-trifluoromethoxy-2,3-dihydro-5H-[1,5]benzothiazepin-4-one are thus obtained in the form of a white solid melting at 188° C.

2-Amino-6-trifluoromethoxybenzothiazole may be obtained by the method described by L. M. YAGUPOL'SKII et al., Zh. Obshch. Khim., 33 (7), 2301 (1963).

EXAMPLE 7

The procedure is carried out as in Example 1, but starting with 1.2 g of bromine in 2 ml of acetic acid, 2.5 g of 4-benzyl-7-trifluoromethoxy-4,5-dihydro-1H,2H-[1,4]benzodiazepin-3-one and 1.6 g of potassium thiocyanate in 25 ml of acetic acid. The product obtained is chromatographed under nitrogen pressure (150 kPa) on 75 g of 20–45 μm silica gel contained in a column 2.5 cm in diameter, eluted with ethyl acetate. 0.6 g of the product obtained (out of 2.25 g obtained in total) is dissolved in 45 ml of ethanol, to which 0.1 ml of methanesulphonic acid is added. After stirring for 3 hours at 20° C., the solution is concentrated to dryness under reduced pressure (2 kPa). The product obtained is suspended in ethyl ether, separated by filtration, washed with ethyl ether and dried under reduced pressure (2 kPa) at 20° C. 0.74 g of 6-benzyl-2-imino-9-trifluoromethoxy-6,7-dihydro-4H-thiazolo[3,4,5-kj][1,4]benzodiazepin-5-one methanesulphonate is thus obtained in the form of a cream-coloured solid melting at a temperature greater than 260° C. [analysis $C_{19}H_{18}F_3N_3O_5S_2$. % calculated C: 46.62, H: 3.71, F: 11.64, N: 8.58, O: 16.34, S: 13.10, % found C: 46.5, H: 3.4, F: 11.3, N: 8.5, S: 12.6].

EXAMPLE 8

The procedure is carried out as in Example 1, but using 4.15 g of bromine in 5 ml of acetic acid, 8.3 g of 4-benzyl-7-trifluoromethoxy-2,3,4,5-tetra-hydro-1H-[1,4]benzodiazepine in 120 ml of acetic acid and 10 g of potassium thiocyanate. 2.7 g of a brown oil are obtained, which oil is chromatographed successively on silica gel and then on neutral alumina deactivated with 10% water, eluting in both cases with a mixture of ethyl acetate and cyclohexane (50-50 by volume). The product obtained (0.68 g) is dissolved in 45 ml of ethanol, to which 0.23 ml of methanesulphonic acid is added. After stirring for 2 hours at 20° C., the solution is concentrated to dryness under reduced pressure (2 kPa). The product obtained is suspended in ethanol, separated by filtration, washed with ethanol and then ethyl ether and dried under reduced pressure (2 kPa) at 20° C. 0.32 g of 6-benzyl-2-imino-9-trifluoromethoxy-4,5,6,7-tetrahydro-2H-thiazolo[3,4,5-kj][1,4]benzodiazepine dimethanesulphonate is obtained in the form of a beige solid melting at a temperature greater than 260° C. [analysis $C_{20}H_{24}F_3N_3O_7S_3$, % calculated C: 42.02, H: 4.23, F: 9.97, N: 7.35, O: 19.59, S: 16.83, % found C: 41.2, H: 4.2, F: 9.3, N: 7.2, S: 16.5].

4-Benzyl-7-trifluoromethoxy-2,3,4,5-tetra-hydro-1H-[1,4]benzodiazepine may be prepared as in Example 6, but using 95 ml of lithium tetrahydroaluminate solution (about 0.35 M) in tetrahydrofuran and 6 g of 4-benzyl-7-trifluoromethoxy-4,5-dihydro-1H,3H-[1,4]benzodiazepin-2-one in 40 ml of anhydrous tetrahydrofuran. 4.8 g of 4-benzyl-7-trifluoromethoxy-2,3,4,5-tetrahydro-1H-1,4-benzodiazepine are obtained in the form of a colourless oil [$^1$H NMR spectrum in DMSO-$d_6$, T=300K, δ in ppm (300 Mhz): 2.75 (2H, m, NCH$_2$) 3.00 (2H, m, NCH$_2$); 3.58 (2H, s, CH$_2$); 3.63 (2H, s, CH$_2$); 5.65 (1H, t, J=2Hz, NH); 6.80 (1H, d, J=2Hz, CH); 6.90 (1H, d, J=8Hz, CH); 7.00 (1H, dd, J=8 and 2Hz, CH); 7.30 (5H, m, 5 aryl CH)].

4-Benzyl-7-trifluoromethoxy-4,5-dihydro-1H,3H-[1,4] benzodiazepin-2-one and 4-benzyl-7-trifluoromethoxy-4,5-dihydro-1H,2H-[1,4]benzodiazepin-3-one may be prepared in the following manner: 16.5 g of chloroacetyl chloride are added to a solution, kept at a temperature close to 20° C., of 15.1 g of 2-benzylamino-methyl-4-trifluoromethoxyaniline in 350 ml of ethyl ether, followed by 350 ml of a saturated aqueous sodium hydrogen carbonate solution. The reaction mixture is stirred for 1 hour at the same temperature. The insoluble matter is then removed by filtration and the organic phase dried over magnesium sulphate, filtered and concentrated to dryness under vacuum (2 kPa). The evaporation residue is dissolved in 300 ml of a tetrahydrofuran/isopropyl alcohol (50/50 by volume) mixture to which 17.6 g of potassium tert-butoxide are added and the mixture is stirred for 1 hour at a temperature close to 20° C. After acidification with 12 ml of acetic acid and dilution with 350 ml of distilled water, the mixture is extracted twice with 100 ml of ethyl acetate and the combined organic phases are dried over magnesium sulphate, filtered and concentrated to dryness under vacuum (2 kPa). The oil obtained is taken up in 50 ml of a cyclohexane and ethyl acetate mixture (75/25 by volume) where a solid crystallizes. The latter is separated by filtration, washed with 10 ml of this same mixture and yields 6.04 g of 4-benzyl-7-trifluoromethoxy-4,5-dihydro-1H,3H-[1,4]benzodiazepin-2-one in the form of a white solid melting at 178° C. The filtrate is concentrated to dryness under vacuum (2 kPa) and the residue is chromatographed on 160 g of 20–45 μm silica contained in a column 3.5 cm in diameter, eluting with an ethyl acetate/cyclohexane (50/50 by volume) mixture. 5.72 g of 4-benzyl-7-trifluoromethoxy-4,5-dihydro-1H,2H-[1,4]benzodiazepin-3-one are thus obtained in the form of a white solid melting at 124° C.

2-Benzylaminomethyl-4-trifluoromethoxyaniline may be prepared in the following manner: 100 ml of anhydrous 1,4-dioxane are added to 97 ml of a 1 M solution of lithium tetrahydroaluminate in tetrahydrofuran, kept under argon at around 20° C., followed dropwise by a solution of 15 g of N-benzyl-2-amino- 5-trifluoromethoxybenzamide in 70 ml of anhydrous 1,4-dioxane, and the mixture is stirred for 24 hours under reflux. After hydrolysis, at around 5° C., by a slow addition of 20 ml of distilled water, the insoluble matter appearing is separated by filtration, washed with distilled water and then with ethyl acetate and removed. The filtrate is separated after settling out and the organic phase is dried over magnesium sulphate and concentrated to dryness under reduced pressure (2 kPa). The product obtained is chromatographed under nitrogen pressure (150 kPa) on 150 g of 20–45 μm silica gel contained in a column 3.5 cm in diameter, eluting with a mixture of cyclohexane and ethyl acetate (75-25 by volume). 7.39 g of 2-benzylaminomethyl-4-trifluoromethoxyaniline are thus obtained in the form of a colourless oil [$^1$H NMR spectrum in DMSO-$d_6$, T=300K, δ in ppm (300 Mhz): 2.65 (1H, s, NH), 3.65 (2H, s, NCH$_2$) 3.72 (2H, s, NCH$_2$), 5.40 (2H, s, NH$_2$), 6.70 (1H, d, J=8 Hz, arom. CH), 6.98 (1H, d, J=8 Hz, arom. CH), 7.04 (1H, s, arom. CH), between 7.20 and 7.50 (5H, m, aromatic 5CH)].

N-Benzyl-2-amino-5-trifluoromethoxybenzamide may be prepared in the following manner: a solution of 5 g of N-benzyl-2-tert-butoxycarbonylamino-5-trifluoromethoxybenzamide in 25 ml of trifluoroacetic acid is stored for 16 hours at a temperature close to 20° C., and then concentrated to dryness under reduced pressure (2 kPa). The product obtained is dissolved in ethyl acetate and the solution is washed successively with twice 15 ml of distilled water and 15 ml of a saturated aqueous sodium hydrogen carbonate solution, and then concentrated to dryness under reduced pressure (2 kPa). The product obtained is suspended in pentane, separated by filtration and dried under reduced pressure (2 kPa). 3.55 g of N-benzyl-2-amino-5-trifluoromethoxybenzamide are thus obtained in the form of a cream-coloured solid melting at 143° C.

N-Benzyl-2-tert-butoxycarbonylamino-5-trifluoromethoxybenzamide may be prepared in the following manner: 12.9 g of N,N'-dicyclohexylcarbodiimide are added to a solution, kept under an argon atmosphere at −10° C., of 20 g of 2-tert-butoxycarbonylamino-5-trifluoromethoxybenzoic acid, 16.9 g of 1-hydroxybenzotriazole and 6.8 g of benzylamine in 400 ml of anhydrous tetrahydrofuran. The mixture is stirred for 2 hours at the same temperature and then for 16 hours at a temperature close to 20° C. After cooling to 0° C., the insoluble matter is separated by filtration, washed with ethyl acetate and the filtrate is concentrated to dryness under reduced pressure (2 kPa). The product obtained is dissolved in 60 ml of ethyl acetate and the solution is washed twice with 25 ml of a saturated aqueous sodium hydrogen carbonate solution, dried over magnesium sulphate and concentrated to dryness under reduced pressure (2 kPa). The product obtained is resuspended in a mixture of petroleum ether and pentane (50-50 by volume), separated by filtration, washed with the mixture of petroleum ether and pentane and dried under reduced pressure (2 kPa). 21.7 g of N-benzyl-2-tert-butoxy-carbonylamino-5-trifluoromethoxybenzamide are thus obtained in the form of a cream-coloured solid melting at 144° C.

2-tert-Butoxycarbonylamino-5-trifluoromethoxybenzoic acid may be prepared in the following manner: 168 ml of a 1.5 M solution of tert-butyllithium in pentane are added dropwise over 1 hour to a solution, kept at −70° C. under an argon atmosphere, of 29 g of tert-butyl 4-trifluoromethoxyphenylcarbamate in 300 ml of anhydrous tetrahydrofuran. The mixture is stirred for 3 hours 30 minutes at −20° C., cooled again to around −70° C. and an excess of solid carbon dioxide dried over anhydrous tetrahydrofuran is added in small quantities. The mixture is stirred for 16 hours at a temperature close to 20° C. and then 500 ml of a saturated aqueous ammonium chloride solution and 200 ml of ethyl acetate are added. The aqueous phase is extracted twice with 200 ml of ethyl acetate and the organic extracts are combined, dried over magnesium sulphate and concentrated to dryness under reduced pressure (2 kPa). The product obtained is suspended in a mixture of petroleum ether and pentane (50-50 by volume), separated by filtration, washed with pentane and dried under reduced pressure (2 kPa). 31.7 g of 2-tert-butoxycarbonylamino-5-trifluoromethoxybenzoic acid are thus obtained in the form of a cream-coloured solid melting between 204–208° C.

EXAMPLE 9

The procedure is carried out as in Example 1, but starting with 1.5 g of bromine in 5 ml of acetic acid, 2.34 g of 7-trifluoromethoxy-1,2,3,5-tetrahydro-[4,1]benzothiazepine, 2.5 g of potassium thiocyanate and 20 ml of acetic acid. The product obtained (3.42 g) is chromatographed under nitrogen pressure (150 kPa) on 80 g of 20–45 μm silica gel contained in a column 2.5 cm in diameter eluting with a mixture of ethyl acetate and cyclohexane (50-50 by volume). The product obtained is concreted by trituration in 5 ml of petroleum ether, separated by filtration and dried under reduced pressure (2 kPa). The product obtained (0.66 g) is dissolved in 30 ml of ethanol, to which 0.15 ml of methanesulphonic acid is added. After stirring for 16 hours at 20° C., the solution is concentrated to dryness under reduced pressure (2 kPa). The product obtained is recrystallized from 10 ml of a mixture of ethanol and isopropyl ether (75-25 by volume). 0.28 g of 2-imino-9-trifluoromethoxy-4,5-dihydro-2H,7H-thiazolo[3,4,5-de][4,1]benzothiazepine methanesulphonate is thus obtained in the form of a yellow solid melting at a temperature greater than 260° C. [analysis $C_{12}H_{13}F_3N_2O_4S_3$, % calculated C: 35.82, H: 3.26, F: 14.16, N: 6.96, O: 15.9, S: 23.9, % found C 35.6, H: 3.0, F: 14.1, N: 6.9, S: 23.7].

7-Trifluoromethoxy-1,2,3,5-tetrahydro[4,1]benzothiazepine may be prepared in the following manner: the procedure is carried out as in Example 6, but starting with 3.4 g of 7-trifluoromethoxy-1,5-dihydro-3H-[4,1]benzothiazepin-2-one in 25 ml of anhydrous tetrahydrofuran, 15.5 ml of a 1 M solution of lithium tetrahydroaluminate in tetrahydrofuran and 15 ml of anhydrous 1,4-dioxane. 2.34 g of 7-trifluoromethoxy-1,2,3,5-tetrahydro[4,1]benzothiazepine are thus obtained in the form of a yellowish oil [$^1$H NMR spectrum in DMSO-$d_6$, T=300K, δ in ppm (300 Mhz): 2.80 (2H, m, $SCH_2$), 3.25 (2H, m, $NCH_2$), 3.75 (2H, s, $SCH_2$-aryl), 5.60 (1H, t, J=5 Hz, NH), 7.05 (2H, m, 2 arom. CH), 7.20 (1H, s, arom. CH)].

7-Trifluoromethoxy-1,5-dihydro-3H-[4,1]benzothiazepin-2-one may be prepared in the following manner: 47 ml of a 1.5 M solution of tert-butyllithium in pentane are added dropwise over 1 hour to a solution, kept at −70° C. under an argon atmosphere, of 10.3 g of tert-butyl 2-methyl-4-trifluoromethoxyphenylcarbamate in 150 ml of anhydrous tetrahydrofuran. The mixture is stirred for 2 hours at −20° C., cooled to around −70° C., supplemented with 1.1 g of sulphur, and then stirred for 1 hour at −20° C. The mixture is cooled to around −70° C., supplemented with 5.4 g of methyl bromoacetate, and then stirred for 16 hours at a temperature close to 20° C. After hydrolysis with 50 ml of distilled water, the mixture is extracted with three times 50 ml of ethyl acetate. The combined organic extracts are dried over magnesium sulphate and concentrated to dryness under reduced pressure (2 kPa). The product obtained is dissolved in 50 ml of dichloromethane and then 15 ml of trifluoroacetic acid are added. After stirring for 2 hours at a temperature close to 20° C., the mixture is concentrated to dryness under reduced pressure (2 kPa). The product obtained is dissolved in 40 ml of ethyl acetate and the solution is washed with 40 ml of distilled water, dried over magnesium sulphate and concentrated to dryness under reduced pressure (2 kPa). The product obtained is suspended in isopropyl ether, separated by filtration, washed with the same solvent and dried under reduced pressure (2 kPa). 3.45 g of 7-trifluoromethoxy-1,5-dihydro-3H-[4,1]benzothiazepin-2-one are thus obtained in the form of a cream-coloured solid melting at 190° C.

tert-Butyl 2-methyl-4-trifluoromethoxyphenyl carbamate may be prepared in the following manner: 106 ml of a 1.5 M solution of tert-butyllithium in pentane are added dropwise over 1 hour to a solution, kept at −70° C. under an argon atmosphere, of 20 g of tert-butyl 4-trifluoromethoxyphenylcarbamate in 250 ml of anhydrous tetrahydrofuran. The mixture is stirred for 4 hours at −20° C., cooled to around −70° C., supplemented with 10.3 g of iodomethane and then stirred for 16 hours at a temperature close to 20° C. After hydrolysis with 100 ml of distilled water, the mixture is extracted with three times 60 ml of ethyl acetate. The combined organic extracts are dried over magnesium sulphate and concentrated to dryness under reduced pressure (2 kPa). The product obtained is suspended in petroleum ether, separated by filtration, washed with the same solvent and dried under reduced pressure (2 kPa). 15.1 g of tert-butyl 2-methyl-4-trifluoromethoxyphenylcarbamate are thus obtained in the form of a light orange-coloured solid melting at 98° C.

EXAMPLE 10

The procedure is carried out as in Example 1, but starting with 1.6 g of bromine in 5 ml of acetic acid, 2.3 g of 7-trifluoromethyl-1,2,3,5-tetrahydro-[4,1]benzothiazepine, 2.1 g of potassium thiocyanate and 30 ml of acetic acid. After recrystallization from absolute ethanol, 1.15 g of 2-imino-9-trifluoromethyl-4,5-dihydro-2H,7H-thiazolo[3,4,5-de][4,1]benzothiazepine methanesulphonate are obtained in the form of a white solid melting at a temperature greater than 260° C. [analysis $C_{12}H_{13}F_3N_2O_3S_3$, % calculated C: 37.3, H: 3.39, F: 14.75, N: 7.25, O: 12.42, S: 24.89, % found C: 37.2, H: 3.2, F: 14.4, N: 7.2, S: 24.6].

7-Trifluoromethyl-1,2,3,5-tetrahydro-[4,1]benzothiazepine may be prepared in the following manner: the procedure is carried out as in Example 6, but starting with 3.6 g of 7-trifluoromethyl-1,5-dihydro-3H-[4,1]benzothiazepin-2-one in 50 ml of anhydrous tetrahydrofuran and 50 ml of anhydrous 1,4-dioxane and 17.5 ml of a 1 M solution of lithium tetrahydroaluminate in tetrahydrofuran. 2.4 g of 7-trifluoromethyl-1,2,3,5-tetrahydro-[4,1]benzothiazepine are thus obtained in the form of a beige solid melting at 94° C.

7-Trifluoromethyl-1,5-dihydro-3H-[4,1]benzothiazepin-2-one may be prepared in the following manner: a mixture of 14.3 g of methyl (2-tert-butoxycarbonylamino-5-trifluoromethylbenzylsulphanyl)acetate in 50 ml of dichloromethane and 15 ml of trifluoroacetic acid is stirred for 3 hours 30 minutes at a temperature close to 20° C. The mixture is concentrated to dryness under reduced pressure (2 kPa) and the product obtained is dissolved in 40 ml of N,N-dimethylformamide and heated under reflux for 3 hours. The mixture is concentrated to dryness under reduced pressure (2 kPa). The product obtained is dissolved in 50 ml of ethyl acetate and the solution is washed with twice 100 ml of distilled water, dried over magnesium sulphate and concentrated to dryness under reduced pressure (2 kPa). The product obtained is suspended in isopropyl ether, separated by filtration, washed with a mixture of ethyl acetate and cyclohexane (50-50 by volume) and dried under reduced pressure (2 kPa). 3.7 g of 7-trifluoromethyl-1,5-dihydro-3H-[4,1]benzothiazepin-2-one are obtained in the form of a beige solid melting at 239° C.

Methyl (2-tert-butoxycarbonylamino-5-trifluoromethylbenzylsulphanyl)acetate may be prepared in the following manner: 67 ml of a 1.5 M solution of tert-butyllithium in pentane are added dropwise over 1 hour 15 minutes to a solution, kept at −70° C. under an argon atmosphere, of 13.7 g of tert-butyl 2-methyl-4-trifluoromethylphenylcarbamate in 180 ml of anhydrous tetrahydrofuran. The mixture is stirred for 3 hours at −20°

C., cooled to around −70° C., supplemented with 1.6 g of sulphur, and then stirred for 1 hour at −20° C. The mixture is cooled to around −40° C., supplemented with 7.6 g of methyl bromoacetate, and then stirred for 16 hours at a temperature close to 20° C. After hydrolysis with 300 ml of distilled water, the mixture is extracted twice with a total of 160 ml of ethyl acetate. The combined organic extracts are dried over magnesium sulphate and concentrated to dryness under reduced pressure (2 kPa). The product obtained is dissolved in petroleum ether and the solution is filtered and then concentrated to dryness under reduced pressure (2 kPa). 14.3 g of methyl (2-tert-butoxycarbonylamino-5-trifluoromethylbenzylsulphanyl)acetate are obtained in the form of a yellow solid melting at 54° C. [$^1$H NMR spectrum in DMSO-$d_6$, T=300K, δ in ppm (300 Mhz): 1.45 (9H, s, $CH_3)_3$), 3.25 (2H, S, $SCH_2CO$), 3.60 (3H, s, O $CH_3$), 4.00 (2H, s, $SCH_2$-aryl), 7.60 (2H, m, 2 arom. CH), 7.85 (1H, d, J=7 Hz, arom. CH), 8.85 (1H, s, NH)].

Methyl (2-tert-butoxycarbonylamino-5-trifluoromethylbenzylsulphanyl)acetate may also be prepared by the following method: 14 g of methyl thioglycolate are poured over a suspension of 5.2 g of sodium hydride (80% dispersion in liquid paraffin) in 59 ml of dimethylformamide, cooled to 0° C. and kept under a nitrogen atmosphere and the mixture is then stirred for 1 hour 30 min at a temperature close to 20° C. A solution of 37.8 g of tert-butyl 2-bromomethyl-4-trifluoromethylphenylcarbamate in 30 ml of dimethylformamide is then poured in and the mixture is stirred for 16 hours. The reaction medium is concentrated to dryness under vacuum (2 kPa) and the paste obtained is taken up in 200 ml of distilled water and extracted three times with 50 ml of ethyl acetate. The combined organic phases are dried over magnesium sulphate, filtered and concentrated to dryness under vacuum (2 kPa). The oil (32.6 g) is chromatographed on 360 g of 20–45 μm silica contained in a column 4 cm in diameter, eluting with a cyclohexane/ethyl acetate (90/10 by volume) mixture. 15.2 g of methyl (2-tertbutoxycarbonylamino-5-trifluoromethylbenzylsulphanyl)acetate are thus obtained in the form of a yellow solid melting at 54° C.

tert-Butyl 2-methyl-4-trifluoromethylphenylcarbamate is prepared in the following manner: 154 ml of a 1.5 M solution of tert-butyllithium in pentane are added dropwise over 1 hour to a solution, kept at −70° C. under an argon atmosphere, of 30 g of tert-butyl 4-trifluoromethylphenylcarbamate in 390 ml of anhydrous tetrahydrofuran. The mixture is stirred for 4 hours at −20° C., cooled to about −70° C., supplemented with 16.4 g of iodomethane and then stirred for 16 hours at a temperature close to 20° C. After hydrolysis with 300 ml of distilled water, the mixture is extracted with twice 160 ml of ethyl acetate in total. The combined organic extracts are dried over magnesium sulphate and concentrated to dryness under reduced pressure (2 kPa). The product obtained is suspended in petroleum ether, separated by filtration, washed with the same solvent and dried under reduced pressure (2 kPa). 20.5 g of tert-butyl 2-methyl-4-trifluoromethylphenylcarbamate are thus obtained in the form of a beige solid melting at 101° C.

tert-Butyl 2-bromomethyl-4-trifluoromethylphenylcarbamate may be prepared in the following manner: a mixture of 40 g of tert-butyl 2-methyl-4-trifluoromethylphenylcarbamate, 26 g of N-bromosuccinimide and 1.5 g of benzoyl peroxide in 290 ml of carbon tetrachloride is heated to boiling temperature and it is illuminated with a 100 W Mazdasol lamp for 4 hours. The succinimide formed is removed by filtration and the filtrate is successively washed with 500 ml of distilled water, 200 ml of saturated sodium hydrogen carbonate solution and then 200 ml of distilled water, dried over magnesium sulphate, filtered and concentrated to dryness under vacuum (2 kPa). The oil is taken up in petroleum ether and the crystals obtained are separated by filtration. 37.9 g of tert-butyl 2-bromomethyl-4-trifluoromethylphenylcarbamate are thus obtained in the form of a white solid melting at 98° C.

EXAMPLE 11

The procedure is carried out as in Example 4, but starting with 6.35 g of 2-imino-9-trifluoromethyl-4,5-dihydro-2H,7H-thiazolo[3,4,5-de][4,1]benzothiazepine and 15.1 g of 3-chloroperbenzoic acid (80% purity) in 130 ml of dichloromethane. 4.12 g of 2-imino-9-trifluoromethyl-4,5-dihydro-2H,7H-thiazolo-[3,4,5-de][4,1]benzothiazepine 6,6-dioxide methanesulphonate are thus obtained in the form of a white powder melting at a temperature greater than 260° C. [analysis $C_{12}H_{13}F_3N_2O_5S_3$, % calculated C: 34.45, H: 3.13, F: 13.62, N: 6.69, S: 22.99, % found C: 34.46, H: 2.94, F: 13.17, N: 6.71, S: 23.11].

EXAMPLE 12

The procedure is carried out as in Example 5, but starting with 230 mg of 2-imino-9-trifluoromethyl-4,5-dihydro-2H,7H-thiazolo[3,4,5-de][4,1]benzothiazepine and 198 mg of 3-chloroperbenzoic acid (80% purity) in 8 ml of dichloromethane. 210 mg of (R,S)-2-imino-9-trifluoromethyl-4,5-dihydro-2H,7H-thiazolo[3,4,5-de][4,1]benzothiazepine 6-oxide methanesulphonate are thus obtained in the form of a white powder melting at a temperature greater than 260° C. [analysis $C_{12}H_{13}F_3N_2O_4S_3$, % calculated C: 35.82, H 3.26, F: 14.16, N 6.96, S: 23.9, % found C 36.2, H: 2.9, F 13.9, N: 7.0, S: 23.5].

EXAMPLE 13

400 mg of (R,S)-2-imino-9-trifluoromethyl-4,5-dihydro-2H,7H-thiazolo[3,4,5-de][4,1]benzothiazepine 6-oxide are dissolved in 160 ml of dichloromethane and the mixture is injected onto 700 g of (S,S) WHELCK-01® type chiral stationary phase contained in a column 60 mm in diameter and 400 mm in length, eluting with a dichloromethane/n-heptane/methanol (50/50/2 by volume) mixture with a flow rate of 70 ml/min. 200 mg of (+)-2-imino-9-trifluoromethyl-4,5-dihydro-2H,7H-thiazolo[3,4,5-de][4,1]benzohiazepine 6-oxide ([α]°=+27.7°±1° c=0.2% methanol) and 200 mg of (−)-2-imino-9-trifluoromethyl-4,5-dihydro-2H,7H-thiazolo[3,4,5-de][4,1]benzothiazepine 6-oxide ([α]°=−28.2°±1°, c=0.2% methanol) are obtained.

200 mg of (+)-2-imino-9-trifluoromethyl-2H,7H-thiazolo[3,4,5-de][4,1]benzothiazepine 6-oxide are dissolved in 30 ml of ethanol with 70 mg of methanesulphonic acid and the mixture is stirred for 16 hours at a temperature close to 20° C. The medium is then concentrated to dryness under vacuum (2 kPa) and the colourless lacquer is taken up in 10 ml of acetone. The solid is separated by filtration, washed with twice 2 ml of acetone. 240 mg of (+)-2-imino-9-trifluoromethyl-2H,7H-thiazolo[3,4,5-de][4,1]benzothiazepine 6-oxide methanesulphonate are obtained in the form of a white solid melting at 230° C. (sticky melting) [analysis $C_{12}H_{13}F_3N_2O_4S_3$ % calculated C: 35.82, H: 3.26, F: 14.16, N: 6.96, S: 23.9, % found C: 35.51, H 2.78, F: 14.26, N: 6.75, S: 23.95; [α]°=+73.1°±1.1°c=0.5% methanol]

200 mg of (−)-2-imino-9-trifluoromethyl-4,5-dihydro-2H,7H-thiazolo[3,4,5-de][4,1]benzothiazepine 6-oxide are dissolved in 30 ml of ethanol with 70 mg of methanesulphonic acid and the mixture is stirred for 16 hours at a temperature close to 20° C. The medium is then concentrated to dryness under vacuum (2 kPa) and the colourless lacquer is taken up in 10 ml of acetone. The solid is separated by filtration, washed with twice 2 ml of acetone, and 230 mg of (−)-2-imino-9-trifluoromethyl-4,5-dihydro-2H,7H-thiazolo[3,4,5-de][4,1]benzothiazepine 6-oxide methanesulphonate are obtained in the form of a white solid melting at 235° C. (sticky melting) [analysis $C_{12}H_{13}F_3N_2O_4S_3$ % calculated C: 35.82, H: 3.26, F: 14.16, N: 6.96, S: 23.9, % found C: 35.70, H: 3.14, F: 13.30, N: 6.91, S: 24.23; $[\alpha]°=-74.2°\pm1.2°$ c=0.5% in methanol].

EXAMPLE 14

0.92 g of 3-chloroperbenzoic acid (80% purity) is added to a solution, under argon and cooled to 0° C., of 1.2 g of 2-imino-9-trifluoromethyl-5,6-dihydro-2H,4H-thiazolo[3,4,5-ef][1,5]benzothiazepine in 20 ml of dichloromethane. The mixture is stirred for 1 hour 30 minutes at the same temperature. After chromatography, eluting with ethyl acetate, and treating with methanesulphonic acid, 0.88 g of 2-imino-9-trifluoromethyl-5,6-dihydro-2H,4H-thiazolo[3,4,5-ef ][1,5]benzothiazepine 7-oxide methanesulphonate is obtained in the form of a white solid melting at a temperature greater than 260° C. [analysis $C_{12}H_{13}F_3N_2O_4S_3$ % calculated C: 35.82, H: 3.26, F: 14.16, N: 6.96, O: 15.9, S 23.9, % found C: 35.7, H: 3.3, F: 13.8, N: 6.9, S: 24.0].

EXAMPLE 15

The procedure is carried out as in Example 4, but starting with 1 g of 2-imino-9-trifluoromethyl-5,6-dihydro-2H,4H-thiazolo[3,4,5-ef][1,5]benzothiazepine and 2.2 g of 3-chloroperbenzoic acid (80% purity) in 20 ml of dichloromethane. 789 mg of 2-imino-9-trifluoromethyl-5,6-dihydro-2H,4H-thiazolo[3,4,5-ef ][1,5]benzothiazepine 6,6-dioxide methanesulphonate are thus obtained in the form of a white powder melting at a temperature greater than 260° C. [Analysis $C_{12}H_{13}F_3N_2O_5S_3$% calculated C: 34.45, H: 3.13, F: 13.62, N: 6.69, S 22.99, % found C: 34.16, H 3.17, F: 13.56, N 6.75, S: 23.23].

EXAMPLE 16

The procedure is carried out as in Example 1, but using 6.3 g of bromine in 20 ml of acetic acid, 9 g of 8-trifluoromethyl-2,3,4,5-tetrahydro-[1,5]benzothiazepine trifluoroacetate, 8.3 g of potassium thiocyanate and 90 ml of acetic acid. The product obtained (6.96 g) is chromatographed under nitrogen pressure (150 kPa) on 90 g of 20–45 μm silica gel contained in a column 3 cm in diameter, eluting with a mixture of ethyl acetate and cyclohexane (50-50 by volume). 4.4 g of the product obtained (out of 5.7 g obtained in total) are dissolved in 80 ml of ethanol, to which 1.5 ml of methanesulphonic acid are added. 5 g of 2-imino-9-trifluoromethyl-5,6-dihydro-2H, 4H-thiazolo[3,4,5-ef][1,5]benzothiazepine methanesulphonate are thus obtained in the form of a white solid melting at a temperature greater than 260° C. [analysis $C_{12}H_{13}F_3N_2O_3S_3$, % calculated C: 37.3, H: 3.39, F: 14.75, N: 7.25, O: 12.42, S: 24.89, % found C: 37.4, H: 3.0, F: 14.7, N: 7.3, S: 25.3].

8-Trifluoromethyl-2,3,4,5-tetrahydro-[1,5]benzothiazepine trifluoroacetate may be prepared in the following manner: a solution [lacuna] 15 ml of trifluoroacetic acid is added to a solution of 13 g of tert-butyl 8-trifluoromethyl-2,3,4,5-tetrahydro-[1,5]benzothiazepine-5-carboxylate in 30 ml of dichloromethane. The mixture is stirred for 1 hour at a temperature close to 20° C. and then concentrated to dryness under reduced pressure (2 kPa). The product obtained is dissolved in 60 ml of ethyl acetate and the solution is washed with 100 ml of distilled water, dried over magnesium sulphate and concentrated to dryness under reduced pressure (2 kPa). The product obtained (16.6 g) is chromatographed under nitrogen pressure (150 kPa) on 160 g of 20–45 μm silica gel contained in a column 4 cm in diameter, eluting with a mixture of cyclohexane and ethyl acetate (75-25 by volume). The product obtained is suspended in petroleum ether and separated by filtration. 9 g of 8-trifluoro-methyl-2,3,4,5-tetrahydro-[1,5]benzothiazepine trifluoroacetate are obtained in the form of an orange-coloured solid melting at 60° C.

Tert-butyl 8-trifluoromethyl-2,3,4,5-tetrahydro-[1,5]benzothiazepine-5-carboxylate may be prepared in the following manner: 102 ml of a 1.5 M solution of tert-butyllithium in pentane are added dropwise over 1 hour to a solution, kept at −70° C. under argon, of 20 g of tert-butyl 4-trifluoromethylphenylcarbamate in 250 ml of anhydrous tetrahydrofuran. The mixture is stirred for 4 hours at −20° C., cooled to around −60° C., supplemented with 2.5 g of sulphur and then stirred for 45 minutes at −20° C. The mixture is cooled to around −60° C., supplemented with 15.6 g of 1-chloro-3-iodopropane, and then stirred for 16 hours at a temperature close to 20° C., heated for 7 hours under reflux, and then at a temperature close to 20° C. for 48 hours. The mixture is hydrolysed with 200 ml of distilled water and extracted twice with 180 ml of ethyl acetate in total. The combined organic extracts are dried over magnesium sulphate and concentrated to dryness under reduced pressure (2 kPa). The product is chromatographed under nitrogen pressure (150 kPa) on 450 g of 20–45 μm silica gel contained in a column 6 cm in diameter, eluting with a mixture of cyclohexane and ethyl acetate (90-10 by volume). 13 g of tert-butyl 8-trifluoromethyl-[1,5]benzothiazepine-5-carboxylate are thus obtained in the form of a pale yellow oil [$^1$H NMR spectrum in DMSO-$d_6$, T=300K, δ in ppm (300 Mhz): 1.50 (9H, s, $(CH_3)_3$), 1.95 (2H, m, $CH_2$), 3.05 (2H, t, J=6 Hz, $SCH_2$), 3.70 (2H, t, J=6 Hz, $CH_2Cl$), 7.60 (1H, dd, J=8 and 2 Hz, arom. CH), 7.75 (1H, d, J=2 Hz, arom. CH), 7.85 (1H, d, J=8 Hz, arom. CH), 8.60 (1H, s, NHCO)].

EXAMPLE 17

The procedure is carried out as in Example 1, but starting with 0.660 g of bromine in 5 ml of acetic acid, 1 g of (R,S)-3-methyl-7-trifluoromethyl-1,2,3,5-tetrahydro[4,1]benzothiazepine, 0.864 g of potassium thiocyanate and 15 ml of acetic acid. Before alkalinizing with aqueous ammonia, the insoluble matter is removed by filtration and rinsed with ethyl acetate. The product obtained is chromatographed under nitrogen pressure (150 kPa) on 40 g of 20–45 μm silica gel contained in a column 1.5 cm in diameter, eluting with a mixture of ethyl acetate and cyclohexane (50-50 by volume). The product obtained (730 mg) is dissolved in 10 ml of ethanol, to which 0.277 g of methanesulphonic acid is added. After stirring for 16 hours at a temperature close to 20° C., the solution is concentrated to dryness under reduced pressure (2 kPa). The product obtained is triturated in acetone, filtered, rinsed with acetone and then isopropyl ether and air-dried for 16 hours under a ventilated fume cupboard. 0.834 g of (R,S)-2-imino-5-methyl-9-trifluoromethyl-4,5-dihydro-2H,7H-thiazolo[3,4,5-de][4,1]benzothiazepine methanesulphonate is thus obtained in the form of a white solid melting at a temperature greater than 260° C. [analysis $C_{13}H_{15}F_3N_2O_3S_3$, % calculated C: 38.99, H: 3.78, F: 14.23, N: 7.00, O: 11.99, S: 24.02, % found C: 39.05, H: 3.45, F: 13.94, N: 7.03, S: 24.37].

425 mg of (R,S)-2-imino-5-methyl-9-trifluoromethyl-4,5-dihydro-2H,7H-thiazolo[3,4,5-de][4,1]benzothiazepine methanesulphonate are dissolved in a mixture of 25 ml of ethanol, 0.5 ml of triethylamine and 200 ml of n-heptane and the mixture is injected onto 700 g of CHIRALCEL OJ stationary phase (20 µm) contained in a column 60 mm in diameter and 400 mm in length, eluting with an n-heptane/isopropanol/triethylamine (90/10/0.1 by volume) mixture with a flow rate of 90 ml/min. 150 mg of (+)-2-imino-5-methyl-9-trifluoromethyl-4,5-dihydro-2H,7H-thiazolo[3,4,5-de][4,1]benzothiazepine are obtained in the form of a beige solid melting at 102° C. [([α]°=±105.8°+1.7°, c=0.5% methanol); analysis $C_{12}H_{11}F_3N_2S_2$, % calculated C: 47.36, H: 3.64, F: 18.73, N: 9.20, S: 21.07, % found C: 47.59, H: 3.24, F: 18.44, N: 8.99, S: 20.92] and 150 mg of (−)-2-imino-5-methyl-9-trifluoromethyl-4,5-dihydro-2H,7H-thiazolo[3,4,5-de][4,1]benzothiazepine are obtained in the form of a beige solid melting at 102° C. [([α]°=−103.1°±1.6°, c=0.5% methanol); analysis $C_{12}H_{11}F_3N_2S_2$, % calculated C: 47.36, H: 3.64, F: 18.73, N: 9.20, S: 21.07, % found C: 47.64, H: 3.24, F: 18.37, N: 8.97, S: 20.93].

(R,S)-3-Methyl-7-trifluoromethyl-1,2,3,5-tetrahydro[4,1]benzothiazepine may be prepared in the following manner: 16.5 ml of a 2 M solution of the borane-dimethyl sulphide complex in toluene are added dropwise to a solution of 4.5 g of (R,S)-3-methyl-7-trifluoromethyl-1,2,3,5-tetrahydro[4,1]benzothiazepin-2-one in 120 ml of toluene, and the whole is heated for 1 hour 30 minutes under reflux. After returning to about 20° C., the medium is taken up and stirred for 15 minutes in a saturated sodium hydrogen carbonate solution and then extracted twice with ethyl acetate. The combined organic extracts are dried over magnesium sulphate, filtered and concentrated to dryness under reduced pressure (2 kPa). The product is chromatographed under nitrogen pressure (150 kPa) on 55 g of 20–45 µm silica gel contained in a column 2.5 cm in diameter, eluting with a mixture of 20 cyclohexane and ethyl acetate (80-20 by volume). 2.36 g of (R,S)-3-methyl-7-trifluoromethyl-1,2,3,5-tetrahydro-[4,1]benzothiazepine are thus obtained in the form of a colourless oil which crystallizes in the form of white crystals melting at 62° C.

(R,S)-3-Methyl-7-trifluoromethyl-1,2,3,5-tetrahydro[4,1]benzothiazepin-2-one may be prepared in the following manner: a solution of 13.6 g of methyl (R,S)-2-(2-amino-5-trifluoromethylbenzylsulphanyl)-propionate, 2 g of 4-toluenesulphonic acid and 200 ml of toluene is heated for 48 hours under reflux. After returning to a temperature close to 20° C., a saturated aqueous sodium hydrogen carbonate solution is added and the mixture is extracted twice with ethyl acetate. The combined organic extracts are dried over magnesium sulphate, filtered and concentrated to dryness under reduced pressure (2 kPa). The product obtained is chromatographed under nitrogen pressure (150 kPa) on 150 g of 20–45 µm silica gel contained in a column 3.5 cm in diameter, eluting with a mixture of cyclohexane and ethyl acetate (50-50 by volume) and then pure ethyl acetate. 4.5 g of (R,S)-3-methyl-7-trifluoromethyl-1,2,3,5-tetrahydro[4,1]benzothiazepin-2-one are thus obtained in the form of a beige solid melting at 220° C.

Methyl (R,S)-2-(2-amino-5-trifluoromethylbenzylsulphanyl)propionate may be prepared in the following manner: 20 g of trifluoroacetic acid are added all at once to a solution of 17.3 g of methyl (R,S)-2-(2-tert-butoxycarbonylamino-5-trifluoromethylbenzylsulphanyl)-propionate and 200 ml of dichloromethane and the whole is stirred for 16 hours at a temperature close to 20° C. After concentrating to dryness under reduced pressure (2 kPa), the evaporation residue is taken up in ethyl acetate and a saturated aqueous sodium hydrogen carbonate solution. The alkaline phase is reextracted once with ethyl acetate and the combined organic extracts are dried over magnesium sulphate, filtered and concentrated to dryness under reduced pressure (2 kPa). 13.6 g of methyl (R,S)-2-(2-amino-5-trifluoromethylbenzylsulphanyl)propionate are thus obtained in the form of a brown oil which is used as it is.

Methyl (R,S)-2-(2-tert-butoxycarbonylamino-5-trifluoromethylbenzylsulphanyl)propionate may be prepared as in Example 10, but starting with 15 g of tert-butyl 2-methyl-4-trifluoromethylphenylcarbamate in 210 ml of anhydrous tetrahydrofuran, 91 ml of a 1.5 M tert-butyllithium solution in pentane, 1.75 g of sulphur and 11 g of methyl (R,S)-2-bromopropionate. 17.3 g of methyl (R,S)-2-(2-tert-butoxycarbonylamino-5-trifluoromethylbenzylsulphanyl)propionate are thus obtained in the form of a clear yellow oil which is used as it is.

EXAMPLE 18

The procedure is carried out as in Example 1, but starting with 0.76 g of bromine in 6 ml of acetic acid, 1.3 g of (R,S)-3-carbamoyl-7-trifluoromethyl-1,2,3,5-tetrahydro[4,1]benzothiazepine, 0.912 g of potassium thiocyanate and 11 ml of acetic acid. Before alkalinizing with aqueous ammonia, the insoluble matter is removed by filtration, rinsed with ethyl acetate. The product obtained is chromatographed under nitrogen pressure (150 kPa) on 30 g of 20–45 µm silica gel contained in a column 2.5 cm in diameter, eluting with a mixture of ethyl acetate and cyclohexane (90-10 by volume). The product obtained (560 mg) is recrystallized from 5 ml of acetonitrile and 390 mg of (R,S)-5-carbamoyl-2-imino-9-trifluoromethyl-4,5-dihydro-2H,7H-thiazolo[3,4,5-de][4,1]benzothiazepine are thus isolated in the form of a white solid melting at around 114° C. [analysis $C_{12}H_{10}F_3N_3OS_2$, % calculated C: 43.43, H: 3.02, F: 17.1, N: 12.61, O: 4.80, S: 19.24, % found C: 42.83, H: 2.79, F: 16.68, N: 12.3, S: 19.01].

(R,S)-3-Carbamoyl-7-trifluoromethyl-1,2,3,5-tetrahydro[4,1]benzothiazepine may be prepared in the following manner: 3 g of methyl (R,S)-7-trifluoromethyl-1,2,3,5-tetrahydro[4,1]benzothiazepine-3-carboxylate are dissolved in 20 ml of an approximately 5.6 M solution of ammonia in methanol and the mixture is stirred at a temperature close to 20° C. for 16 hours. The medium is concentrated to dryness under reduced pressure and the dry extract is chromatographed under nitrogen pressure (150 kPa) on 35 g of 20–45 µm silica gel contained in a column 2 cm in diameter, eluting with a mixture of ethyl acetate and cyclohexane (50-50 by volume) and then with pure ethyl acetate. 1.3 g (R,S)-3-carbamoyl-7-trifluoro-methly- 1,2,3,5-tetrahydro[4,1]benzothiazepine are thus obtained in the form of an orange-coloured oil [$^1$H NMR spectrum in DMSO-d, T=300K, δ in ppm (250 Mhz): 3.5 and 3.9 (1H each, m, NCH$_2$), 3.6 and 4.6 (1H each, d, J=16 Hz, SCH$_2$), 3.6 (1H, dd, J=4 and 12 Hz, SCH), 6.4 (1H, m, NH), 6.8 (1H, d, J=7 Hz, arom. CH), 7.1 and 7.5 (1H each, s, CONH$_2$), 7.28 (1H, d, J=7 Hz, arom. CH), 7.32 (1H, s, arom. CH)].

Methyl (R,S)-7-trifluoromethyl-1,2,3,5-tetrahydro[4,1]benzothiazepine-3-carboxylate may be prepared in the following manner: a mixture of 4.7 g of methyl 7-trifluoromethyl-1,5-dihydro[4,1]benzothiazepine-3-carboxylate, 15.55 g of magnesium turnings and 150 ml of methanol is heated to about 40° C. When the reaction starts, the bath is removed and the reaction itself sustains the reflux. At the end of the reflux, the medium is adjusted to a temperature close to 0° C. and 270 ml of 4 M hydrochloric acid are added. The insoluble matter is removed by filtration, rinsed with dichloromethane and the filtrate is separated after settling out. The organic extract is dried over magnesium sulphate, filtered and concentrated to dryness under reduced pressure (2 kPa). 3.07 g of methyl (R,S)-7-trifluoromethyl-1,2,3,5-tetrahydro[4,1]benzothiazepine-3-carboxylate are thus obtained in the form of a brown oil [NMR spectrum in DMSO-$d_6$, T=300K, δ in ppm (250 Mhz): between 3.6 and 4.1 (7H, m, $NCH_2$+SCH+½ $SCH_2$+ $OCH_3$), 4.4 (1H, d, J=16 Hz, ½ $SCH_2$), 6.5 (1H, m, NH), 6.8 (1H, d, J=7 Hz, arom. CH), 7.28 (1H, d, J=7 Hz, arom. CH), 7.32 (1H, s, arom. CH)].

Methyl 7-trifluoromethyl-1,5-dihydro[4,1]-benzothiazepine-3-carboxylate may be prepared in the following manner: 9.25 g of trifluoroacetic acid are slowly added to a solution of 7.05 g of methyl 3-dimethylamino-2-(2-tert-butoxycarbonylamino-5-trifluoromethylbenzylsulphanyl)acrylate and 75 ml of dichloromethane and the whole is stirred for 24 hours at a temperature close to 20° C. The medium is concentrated to dryness under reduced pressure (2 kPa) and the residue is taken up in 100 ml of a saturated aqueous sodium hydrogen carbonate solution and the mixture is extracted with once 200 ml of ethyl acetate. The organic extract is dried over magnesium sulphate, filtered and concentrated to dryness under reduced pressure (2 kPa). 6.1 g of methyl 7-trifluoromethyl-1,5-dihydro[4,1]benzothiazepine-3-carboxylate are thus obtained in the form of an orange-coloured solid melting at 260° C.

Methyl 3-dimethylamino-2-(2-tert-butoxycarbonylamino-5-trifluoromethylbenzylsulphanyl)acrylate may be prepared in the following manner: 15.6 g of tert-butyloxy-bis(dimethylamino)methane are poured into a solution of 11.3 g of methyl (2-tert-butoxycarbonylamino-5-trifluoromethylbenzylsulphanyl)acetate and 230 ml of anhydrous 1,2-dimethoxyethane. The medium is heated for 2 hours under reflux and then stirred for 48 hours at a temperature close to 20° C. The medium is then hydrolysed with 150 ml of a saturated aqueous sodium hydrogen carbonate solution and extracted with 200 ml of ethyl acetate. The organic extract is dried over magnesium sulphate, filtered and concentrated to dryness under reduced pressure (2 kPa). The residue (12.1 g) is chromatographed under nitrogen pressure (150 kPa) on 400 g of 20–45 μm silica gel contained in a column 4.5 cm in diameter, eluting with a mixture of cyclohexane and ethyl acetate (80-20 by volume). 7.05 g of methyl 3-dimethylamino-2-(2-tert-butoxycarbonylamino-5-trifluoromethylbenzylsulphanyl) acrylate are thus obtained in the form of a cream-coloured solid [$^1$H NMR spectrum in DMSO-$d_6$, T=300K, d in ppm (250 MHz): 1.50 (9H, s, $(CH_3)_3$), 2.95 (6H, s, $N(CH_3)_2$), 3.60 (3H, s, $OCH_3$), 3.80 (2H, s, $SCH_2$), 7.30 (1H, d, J=2 Hz, arom. CH), 7.50 (1H, dd, J=2 and 7 Hz, arom. CH), 7.65 (1H, s, ethylenic CH), 7.90 (1H, d, J=7 Hz, arom. CH), 8.90 (1H, s, NH)].

EXAMPLE 19

The procedure is carried out as in Example 1, but starting with 0.34 g of bromine in 3 ml of acetic acid, 0.55 g of 3,3-dimethyl-7-trifluoromethyl-1,2-dihydro-5H-[4,1] benzothiazepine, 0.45 g of potassium thiocyanate and 10 ml of acetic acid. The product obtained is chromatographed under nitrogen pressure (150 kPa) on 40 g of 20–45 μm silica gel contained in a column 2.5 cm in diameter, eluting with a mixture of ethyl acetate and cyclohexane (50-50 by volume). The product obtained (610 mg) is dissolved in 10 ml of ethanol, to which 0.22 g of methanesulphonic acid is added. After stirring for 16 hours at a temperature close to 20° C., the solution is concentrated to dryness under reduced pressure (2 kPa). The product obtained is triturated in a mixture of acetone and isopropyl ether (65-35 by volume), filtered, rinsed with acetone and then isopropyl ether and air-dried for 16 hours under a ventilated fume cupboard. 0.595 g of 5,5-dimethyl-2-imino-9-trifluoromethyl-2H,4H, 7H-thiazolo[3,4,5-de][4,1]benzothiazepine methanesulphonate is thus obtained in the form of a white solid melting at a temperature greater than 260° C. [analysis $C_{14}H_{17}F_3N_2O_3S_3$, % calculated C: 40.57, H: 4.13, F: 13.75, N: 6.76, O: 11.58, S: 23.21, % found C: 40.23, H: 3.63, F: 13.46, N: 6.65, S: 23.6].

3,3-Dimethyl-7-trifluoromethyl-1,2-dihydro-5H-[4,1] benzothiazepine may be prepared in the following manner: to a solution of 1.6 g of 3,3-dime-3,3-Dimethyl-7-trifluoromethyl-1,2-dihydro-5H-[4,1]benzothiazepine may be prepared in the following manner: 7.3 ml of a 2 M solution of borane-dime thyl sulphide complex in toluene are added dropwise to a solution of 1.6 g of 3,3-dimethyl-7-trifluoromethyl-1,5-dihydro[4,1]benzothiazepine-2-one in 80 ml of anhydrous toluene, and the whole is heated for 1 hour under reflux. After returning to around 20° C., the medium is taken up and stirred for 30 min in a saturated sodium hydrogen carbonate solution then extracted twice with ethyl acetate. The combined organic extracts are dried over magnesium sulphate, filtered and concentrated to dryness under reduced pressure (2 kPa). The product is chromatographed under nitrogen pressure (150 kPa) on 100 g of 20–45 μm silica gel contained in a column 2.5 cm in diameter, eluting with a mixture of cyclohexane and ethyl acetate (80-20 by volume). 0.55 g of 3,3-dimethyl-7-trifluoromethyl-1,2-dihydro-5H-[4,1]benzothiazepine is thus obtained in the form of white crystals melting at 142° C.

3,3-Dimethyl-7-trifluoromethyl-1,5-dihydro[4,1] benzothiazepine-2-one may be prepared in the following manner: a solution of 3.9 g of 2-(2-amino-5-trifluoromethylbenzylsulphanyl)-2-methyl-propionic acid and 40 ml of xylene is heated under reflux for 72 hours. The medium is then concentrated to dryness under reduced pressure (2 kPa) and the residue is chromatographed under nitrogen pressure (150 kPa) on 55 g of 20–45 μm silica gel contained in a column 2.5 cm in diameter eluting with a mixture of cyclohexane and ethyl acetate (75-25 by volume). The product obtained is taken up and concreted with isopropyl ether and separated by filtration and then rinsed with isopropyl ether, dried under reduced pressure. 1.47 g of 3,3-dimethyl-7-trifluoromethyl-1,5-dihydro[4,1] benzothiazepin-2-one are thus obtained in the form of a cream-coloured solid melting at 210° C.

2-(2-Amino-5-trifluoromethylbenzylsulphanyl)-2-methylpropionic acid may be prepared in the following manner: a solution of 2.55 g of methyl 2-(2-amino-5-trifluoromethylbenzylsulphanyl)-2-methylpropionate, 0.59 g of potassium hydroxide pellets (85% purity) and 30 ml of absolute ethanol is stirred at a temperature close to 20° C. for 5 days. The medium is then acidified with 18 ml of an approximately 5 M hydrochloric isopropanol solution and the medium is concentrated to dryness under reduced pressure (2 kPa). The residue is taken up in ethyl acetate and the insoluble matter is removed by filtration and rinsed with ethyl acetate. The filtrate is concentrated to dryness under reduced pressure (2 kPa) and the residue obtained is chromatographed under nitrogen pressure (150 kPa) on 50 g of 20–45 μm silica gel contained in a column 2 cm in diameter, eluting with an ethyl acetate and methanol mixture (95-5 by volume). A product is isolated which is taken up in petroleum ether and the product is separated by filtration, rinsed with petroleum ether and dried. 2.2 g of 2-(2-amino-5-trifluoromethylbenzylsulphanyl)-2-methylpropionic acid are thus obtained in the form of a cream-coloured solid melting at 113° C.

Methyl 2-(2-amino-5-trifluoromethylbenzylsulphanyl)-2-methylpropionate may be prepared in the following manner: a solution of 9.2 g of methyl 2-(2-tert-butoxycarbonylamino-5-trifluoromethylbenzylsulphanyl)-2-methylpropionate, 10.3 g of trifluoroacetic acid and 100 ml of dichloromethane is stirred at a temperature close to 20° C. for 72 hours. The medium is concentrated to dryness under reduced pressure (2 kPa) and the residue is taken up in 250 ml of a saturated aqueous sodium hydrogen carbonate solution and extracted twice with ethyl acetate. The combined organic extracts are dried over magnesium sulphate, filtered and concentrated to dryness under reduced pressure (2 kPa) to give an oil which is chromatographed under nitrogen pressure (150 kPa) on 80 g of 20–45 μm silica gel contained in a column 3 cm in diameter, eluting with a mixture of cyclohexane and ethyl acetate (75-25 by volume). 5 g of methyl 2-(2-amino-5-trifluoromethylbenzylsulphanyl)-2-methylpropionate are thus obtained in the form of a yellow oil [$^1$H NMR spectrum in DMSO-d6, T=300K, d in ppm (300 Mhz): 1.49 (6H, s, 2CH$_3$), 3.6 (3H, s, OCH$_3$), 3.8 (2H, s, SCH$_2$), 5.6 (2H, s, NH$_2$), 6.75 (1H, d, J=7 Hz, arom. CH), 7.25 (1H, d, J=7 Hz, arom. CH), 7.35 (1H, s, arom. CH)].

Methyl 2-(2-tert-butoxycarbonylamino-5-trifluoromethylbenzylsulphanyl)-2-methylpropionate may be prepared as in Example 10, but starting with 15 g of tert-butyl 2-methyl-4-trifluoromethylphenylcarbamate in 210 ml of anhydrous tetrahydrofuran, 91 ml of a 1.5 M solution of tert-butyllithium in pentane, 1.75 g of sulphur and 11.9 g of methyl 2-bromo-2-methylpropionate. 9.2 g of methyl 2-(2-tert-butoxycarbonylamino-5-trifluoromethylbenzylsulphanyl)-2-methylpropionate are thus obtained in the form of a colourless oil [$^1$H NMR spectrum in DMSO-d$_6$, T=300K, d in ppm (250 Mhz): 1.56 (6H, s, 2 CH$_3$), 1.57 (9H, s, (CH$_3$)$_3$), 3.6 (3H, s, OCH$_3$), 4.0 (2H, s, SCH$_2$), 7.65 (1H, d, J=7 Hz, arom. CH), 7.75 (2H, m, arom. 2CH), 8.9 (1H, s, NH)].

EXAMPLE 20

(R,S)-5-Hydroxymethyl-2-imino-9-trifluoromethyl-4,5-dihydro-2H,7H-thiazolo[3,4,5-de][4,1]benzothiazepine is prepared in the following manner: 300 mg of sodium tetrahydroborate are added to a solution of 2.5 g of methyl (R,S)-2-imino-9-trifluoromethyl-4,5-dihydro-2H,7H-thiazolo[3,4,5-de][4,1]benzothiazepine-5-carboxylate in 25 ml of absolute ethanol, kept under argon, and the whole is heated under reflux for 5 hours. The medium is then stirred for 16 hours at a temperature close to 20° C., then hydrolysed with 50 ml of distilled water and extracted with 50 ml of ethyl acetate. The organic extract is dried over magnesium sulphate, filtered and concentrated to dryness under reduced pressure (2 kPa). The oil obtained is chromatographed under nitrogen pressure (150 kPa) on 30 g of 20–45 μm silica gel contained in a column 2.5 cm in diameter, eluting with a mixture of cyclohexane and ethyl acetate (50-50 by volume). The solid obtained is taken up in isopropyl ether, separated by filtration and dried under reduced pressure (2 kPa). 40 mg of (R,S)-5-hydroxymethyl-2-imino-9-trifluoromethyl-4,5-dihydro-2H,7H-thiazolo[3,4,5-de][4,1]benzothiazepine are thus obtained in the form of a crude solid melting at 167° C. [analysis C$_{12}$H$_{11}$F$_3$N$_2$OS$_2$, % calculated C: 44.99, H: 3.46, F: 17.79, N: 8.74, O 4.99, S: 20.02, a found C: 44.41, H: 3.01, F: 16.84, N: 8.51, S: 20.4].

EXAMPLE 21

The procedure is carried out as in Example 1, but starting with 1.66 g of bromine in 5 ml of acetic acid, 3 g methyl (R,S)-7-trifluoromethyl-1,2,3,5-tetrahydro[4,1]benzothiazepine-3-carboxylate, 2.2 g of potassium thiocyanate and 30 ml of acetic acid. The product obtained is chromatographed under nitrogen pressure (150 kPa) on 80 g of 20–45 μm silica gel contained in a column 3.5 cm in diameter eluting with a mixture of ethyl acetate and cyclohexane (50-50 by volume). 2.5 g of methyl (R,S)-2-imino-9-trifluoromethyl-4,5-dihydro-2H,7H-thiazolo[3,4,5-de][4,1]benzothiazepine-5-carboxylate are thus obtained in the form of an oil.

EXAMPLE 22

The procedure is carried out as in Example 1, but starting with 1.47 g of bromine in 5 ml of acetic acid, 2 g of 7-trifluoromethyl-1,2,3,5-tetrahydro[4,1]benzoxazepine, 3 g of potassium thiocyanate and 50 ml of acetic acid. After chromatography on silica gel, eluting with a mixture of ethyl acetate and cyclohexane (50-50 by volume) and treating with methanesulphonic acid, 1.79 g of 2-imino-9-trifluoromethyl-4,5-dihydro-2H,7H-thiazolo[3,4,5-de][4,1]benozoxazepine methanesulphonate are obtained in the form of a whitish solid melting at around 258° C. [analysis C$_{12}$H$_{13}$F$_3$N$_2$O$_4$S$_2$, % calculated C: 38.92, H: 3.54, F: 15.39, N: 7.56, 0: 17.28, S: 17.31, % found C: 38.67, H: 3.31, F: 15.02, N: 7.69, S: 17.47].

7-Trifluoromethyl-1,2,3,5-tetrahydro[4,1]benzoxazepine may be prepared in the following manner: 15 ml of a 2 N solution in tetrahydrofuran of the borane-methyl sulphide complex are added dropwise under argon and at a temperature close to 20° C. to a suspension of 2.22 g of 7-trifluoromethyl-1,5-dihydro-3H-[4,1]benzoxazepin-2-one in 100 ml of toluene. The reaction medium is then heated to and kept at the boiling temperature for 1 hour 45 minutes. After cooling to around 20° C., it is hydrolysed with 100 ml of a saturated sodium hydrogen carbonate solution and then extracted with twice 100 ml of ethyl acetate. The combined organic phases are dried over magnesium sulphate and then concentrated in a rotary evaporator. After trituration of the residue in petroleum ether, 2 g of 7-trifluoromethyl-1,2,3,5-tetrahydro[4,1]benzoxazepine are obtained in the form of a yellowish solid melting at around 85° C.

7-Trifluoromethyl-1,5-dihydro-3H-[4,1]benzoxazepin-2-one may be prepared in the following manner: 2.9 g of potassium t-butoxide are added under argon and at a temperature close to 5° C. to a solution of 2.95 g of 2-chloro-N-(2-hydroxymethyl-4-trifluoromethylphenyl)acetamide in 330 ml of tetrahydrofuran. After stirring for 1 hour at this temperature, the reaction medium is hydrolysed with 30 ml of a saturated ammonium chloride solution and then extracted with 150 ml of ethyl acetate. The organic phase is dried over magnesium sulphate and then concentrated in a rotary evaporator. After trituration of the residue in a mixture of ethyl ether and petroleum ether, 2.2 g of 7-trifluoromethyl-1,5-dihydro-3H-[4,1]benzoxazepin-2-one are obtained in the form of a white solid melting at around 183° C. p 2-Chloro-N-(2-hydroxymethyl-4-trifluoromethylphenyl)acetamide may be prepared in the following manner: 2.1 ml of chloroacetyl chloride dissolved in 20 ml of dichloromethane are added under argon and at a temperature close to 5° C. to a solution of 5.54 g of 2-amino-5-trifluoromethylphenylmethanol in 100 ml of dichloromethane and 6 ml of triethylamine. The reaction medium is stirred for 3 hours at around 5° C., and then for 18 hours at room temperature. It is then poured over 100 ml of a saturated sodium hydrogen carbonate solution and then extracted with 200 ml of ethyl ether. The organic phase is dried over magnesium sulphate and then concentrated in a rotary evaporator. After chromatography on a silica gel, eluting with a mixture of cyclohexane and ethyl acetate (65-35 by volume) and trituration of the residue in a mixture of ethyl ether and petroleum ether, 4 g of 2-chloro-N-(2-hydroxymethyl-4-trifluoromethylphenyl)acetamide are obtained in the form of a whitish solid melting at around 92° C.

2-Amino-5-trifluoromethylphenylmethanol may be prepared in the following manner: 7.3 g of sodium borohydride are added under argon and at a temperature close to 5° C. to a solution of 7.3 g of 2-amino-5-trifluoromethylbenzoic acid in 250 ml of tetrahydrofuran, followed by 24 ml of chlorotrimethylsilane. After stirring for 44 hours at room temperature, the reaction mixture is cooled to around 5° C. and then hydrolysed with 100 ml of distilled water and extracted twice with ethyl ether (400 and then 150 ml). The combined organic phases are washed with 100 ml of a 1 N sodium hydroxide solution and then dried over magnesium sulphate and concentrated in a rotary evaporator. 7.9 g of 2-amino-5-trifluoromethylphenylmethanol are thus obtained in the form of a white solid melting at 70° C.

2-Amino-5-trifluoromethylbenzoic acid may be prepared according to the method described by M. L. Carmellino et al., Eur. J. Med. Chem. Chim. Ther., 29 (10), 743 (1994).

The medicaments according to the invention consist of a compound of formula (I) or a salt of such a compound, in the pure state or in the form of a composition in which it is combined with any other pharmaceutically compatible product which may be inert or physiologically active. The medicaments according to the invention may be used by the oral, parenteral, rectal or topical route.

Tablets, pills, powders (gelatin capsules, cachets) or granules may be used as solid compositions for oral administration. In these compositions, the active ingredient according to the invention is mixed with one or more inert diluents such as starch, cellulose, sucrose, lactose or silica under an argon stream. These compositions may also comprise substances other than diluents, for example one or more lubricants such as magnesium stearate or talc, a colourant, a coating (sugar-coated tablets) or a glaze.

Pharmaceutically acceptable solutions, suspensions, emulsions, syrups and elixirs containing inert diluents such as water, ethanol, glycerol, vegetable oils or paraffin oil may be used as liquid compositions for oral administration. These compositions may comprise substances other than diluents, for example wetting, sweetening, thickening, flavouring or stabilizing products.

Sterile compositions for parenteral administration may be preferably aqueous or nonaqueous solutions, suspensions or emulsions. Water, propylene glycol, polyethylene glycol, vegetable oils, in particular olive oil, organic esters for injection, for example ethyl oleate, or other suitable organic solvents may be used as solvent or vehicles. These compositions may also contain adjuvants, in particular wetting, isotonizing, emulsifying, dispersing and stabilizing agents. Sterilization may be performed in a number of ways, for example by aseptizing filtration, by incorporating sterilizing agents into the composition, by irradiation or by heating. They may also be prepared in the form of sterile solid compositions which may be dissolved at the time of use in sterile water or any other sterile medium for injection.

Compositions for rectal administration are suppositories or rectal capsules which contain, in addition to the active product, excipients such as cocoa butter, semisynthetic glycerides or polyethylene glycols.

Compositions for topical administration may be for example creams, lotions, colluria, collutoria, nasal drops or aerosols.

In human therapy, the compounds according to the invention are particularly useful for the treatment and/or prevention of convulsions and diseases linked to glutamatergic transmission. They are in particular useful for treating and/or preventing all ischaemias (such as focal or global ischaemia) following cerebrovascular accidents such as thromboembolic and haemorrhagic stroke, cardiac arrest, arterial hypotension, cardiac, vascular or pulmonary surgery or severe hypoglycaemia. They are also useful in the treatment of the effects caused by anoxia, whether it is perinatal or subsequent to drowning, a high pressure or cerebrospinal lesions. These compounds may also be used to treat or prevent the development of neurodegenerative diseases, of HUNTINGDON's chorea, of ALZHEIMER's disease and other dementias, of amyotrophic lateral sclerosis or of other motor neuron diseases, of olivopontocerebellar atrophy and of PARKINSON's disease. These compounds may also be used against epileptogenic (epilepsy) and/or convulsive manifestations, for the treatment of cerebral or spinal traumas, of traumas linked to degeneration of the inner ear or of the retina, of tinnitus, of anxiety, of depression, of schizophrenia, of TOURETTE's syndrome, of hepatic encephalopathies, of sleep disorders, of attention deficit disorders, of disorders of hormonal conditions (excess secretion of GH or LH, secretion of corticosterone), as analgesics, anti-inflammatory agents, antianoretics, antimigraine drugs, antiemetics and to treat poisoning by neurotoxins, as well as neurological disorders associated with viral diseases such as viral meningitis and encephalitis, AIDS, rabies, measles and tetanus. These compounds are also useful for the prevention of, tolerance to and dependency on the symptoms of withdrawal from drugs and alcohol, and of inhibition of addiction to and of dependency on opiates, barbiturates, amphetamine and benzodiazepines. They may also be used in the treatment of deficiencies linked to mitochrondrial abnormalities such as mitochrondrial myopathy, LEBER's syndrome, WERNICKE's encephalopathy, RETT's syndrome, homocysteinaemia, hyperprolinaemia, hydroxybutyricaminoaciduria, saturnine encephalopathy (chronic lead poisoning) and sulphite oxidase deficiency.

The doses depend on the desired effect, on the duration of treatment and on the route of administration used; they are generally between 10 mg and 100 mg per day by the oral route for an adult with unit doses ranging from 5 mg to 50 mg of active substance.

In general, the doctor will determine the appropriate dosage according to the age, weight and all the other factors which are specific to the subject to be treated.

The following examples illustrate compositions according to the invention:

EXAMPLE A

Gelatin capsules containing 50-mg doses of active product having the following composition are prepared according to the usual technique:

| Compound of formula (I) | 50 mg |
| --- | --- |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing 50-mg doses of active product having the following composition are prepared according to the usual technique:

| Compound of formula (I) | 50 mg |
| --- | --- |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerin, titanium oxide (72-3.5-24.5) qs | |
| 1 finished film-coated tablet of 245 mg | |

EXAMPLE C

An injectable solution containing 10 mg of active product having the following composition is prepared:

| Compound of formula (I) | 10 mg |
| --- | --- |
| Benzoic acid | 80 mg |
| Benzyl alcohol | 0.06 ml |
| Sodium benzoate | 80 mg |
| Ethanol, 95% | 0.4 ml |
| Sodium hydroxide | 24 mg |
| Propylene glycol | 1.6 ml |
| Water qs | 4 ml |

What is claimed is:
1. A compound of formula:

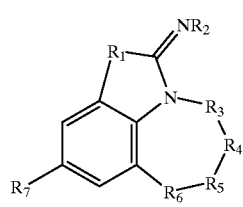

(I)

in which $R_1$ is a sulphur or seleniun atom, $R_2$ is a hydrogen atom or an alkyl radical, —$R_3$—$R_4$—$R_5$—$R_6$— is a chain of formula —$CH_2$—$CH_2$—$CH_2$—$CH_2$—, —$CH_2$—$CH_2$—$CH_2$—CO—,
—$CH_2$—$CH_2$—$CH_2$—$CH(R_8)$—,
—$CH_2$—$CH_2$—$CH_2$—Se—, —$CH_2$—$CH_2$—Se—$CH_2$—,
—$CH_2$—$CH_2$—$CH_2$—S—, —$CH_2$—$CH_2$—$CH_2$—SO—,
—$CH_2$—$CH_2$—$CH_2$—$SO_2$—, —$CH_2$—$CH_2$—$CH_2$—O—,
—$CH_2$—$CH_2$—$CH_2$—$N(R_9)$—,
—$CH_2$—$CH_2$—CO—$CH_2$—, —$CH_2$—$CH_2$—$CH(R_8)$—$CH_2$—,
—$CH_2$—$CH_2$—S—$CH_2$—,
—$CH_2$—$CH_2$—SO—$CH_2$—, —$CH_2$—$CH_2$—$SO_2$—$CH_2$—,
—$CH_2$—C(alk)(alk')—S—$CH_2$—,
—$CH_2$—C(alk)(alk')—SO—$CH_2$—, —$CH_2$—C(alk)(alk')—$SO_2$—$CH_2$—, —$CH_2$—$CH(R_{10})$—S—$CH_2$—,
—$CH_2$—$CH(R_{10})$—SO—$CH_2$—, —$CH_2$—$CH(R_{10})$—$SO_2$—$CH_2$—, —$CH_2$—$CH_2$—O—$CH_2$—,
—$CH_2$—$CH_2$—$N(R_9)$—$CH_2$— or —$CH_2$—CO—$N(R_9)$—$CH_2$—, $R_7$ is a polyfluoroalkyl or polyfluoroalkoxy radical, $R_8$ is a hydroxyl radical, $R_9$ is a hydrogen atom or an alkyl or benzyl radical, $R_{10}$ is an alkyl, —$CH_2OH$, —COOalk, —COOH or —$CONH_2$ radical, alk is an alkyl radical, alk' is an alkyl radical, the alkyl radicals containing 1 to 6 straight- or branched-chain carbon atoms, and, when said compound contains one or more asymmetric centers, its isomers, racemates and enantiomers, and the pharmaceutically acceptable salts of said compound with an inorganic or organic acid.

2. A compound of claim 1 wherein $R_7$ is a trifluoromethoxy or trifluoromethyl radical.

3. A compound of claim 1, wherein $R_1$ is a sulphur atom, $R_2$ is a hydrogen atom, —$R_3$—$R_4$—$R_5$—$R_6$— is a chain of formula —$CH_2$—$CH_2$—$CH_2$—$CH_2$—, —$CH_2$—$CH_2$—$CH_2$—CO—, —$CH_2$—$CH_2$—$CH_2$—$CH(R_8)$—, —$CH_2$—$CH_2$—$CH_2$—Se—, —$CH_2$—$CH_2$—Se—$CH_2$—, —$CH_2$—$CH_2$—$CH_2$—S—, —$CH_2$—$CH_2$—$CH_2$—SO—, —$CH_2$—$CH_2$—$CH_2$—$SO_2$—, —$CH_2$—$CH_2$—$CH_2$—O—, —$CH_2$—$CH_2$—$CH_2$—$N(R_9)$—, —$CH_2$—$CH_2$—CO—$CH_2$—, —$CH_2$—$CH_2$—$CH(R_8)$—$CH_2$—, —$CH_2$—$CH_2$—S—$CH_2$—, —$CH_2$—$CH_2$—SO—$CH_2$—, —$CH_2$—$CH_2$—$SO_2$—$CH_2$—, —$CH_2$—C(alk)(alk')—S—$CH_2$—, —$CH_2$—C(alk)(alk')—SO—$CH_2$—, —$CH_2$—C(alk)(alk')—$SO_2$—$CH_2$—, —$CH_2$—$CH(R_{10})$—S—$CH_2$—, —$CH_2$—$CH(R_{10})$—SO—$CH_2$—, —$CH_2$—$CH(R_{10})$—$SO_2$—$CH_2$—, —$CH_2$—$CH_2$—O—$CH_2$—, —$CH_2$—$CH_2$—$N(R_9)$—$CH_2$— or —$CH_2$—CO—$N(R_9)$—$CH_2$—, $R_7$ is a trifluoromethyl or trifluoromethoxy radical, $R_8$ is a hydroxyl radical, $R_9$ is a hydrogen atom or an alkyl or benzyl radical, $R_{10}$ is an alkyl, —$CH_2OH$, —COOalk, —COOH or —$CONH_2$ radical, alk is an alkyl radical and alk' is an alkyl radical.

4. A compound of claim 1, selected from the group consisting of:

2-imino-9-trifluoromethoxy-4,5,6,7-tetrahydro-2H-thiazolo[5,4,3-jk][1]benzazepin-7-ol, 2-imino-9-trifluoromethoxy-4,5,6,7-tetrahydro-2H-thiazolo[5,4,3-jk][1]benzazepine, 2-imino-9-trifluoromethyl-4,5,6,7-tetrahydro-2H-thiazolo[5,4,3-jk][1]benzazepine, 2-imino-9-trifluoromethoxy-5,6-dihydro-2H,4H-thiazolo[3,4,5-ef][1,5]benzothiazepine 7,7-dioxide 2-imino-9-trifluoromethoxy-5,6-dihydro-2H,4H-thiazolo[3,4,5-ef][1,5]benzothiazepine 7-oxide, 2-imino-9-trifluoromethoxy-5,6-dihydro-2H,4H-thiazolo[3,4,5-ef][1,5]benzothiazepine, 6-benzyl-2-imino-9-trifluoromethoxy-6,7-dihydro-4H-thiazolo[3,4,5-kj][1,4]benzodiazepine-5-one, 6-benzyl-2-imino-9-trifluoromethoxy-4,5,6,7-tetrahydro-2H-thiazolo[3,4,5-kj][1,4]benzodiazepine, 2-imino-9-trifluoromethoxy-4,5-dihydro-2H,7H-thiazolo[3,4,5-de][4,1]benzothiazepine, 2-imino-9-trifluoromethyl-4,5-dihydro-2H,7H-thiazolo[3,4,5-de][4,1]benzothiazepine, 2-imino-9-trifluoromethyl-4,5-dihydro-2H,7H-thiazolo[3,4,5-de][4,1]benzothiazepine 6,6-dioxide, 2-imino-9-trifluoromethyl-5,6-dihydro-2H,4H-thiazolo[3,4,5-ef][1,5]benzothiazepine 7-oxide, 2-imino-9-trifluoromethyl-5,6-dihydro-2H,4H-thiazolo[3,4,5-ef][1,5]benzothiazepine 6,6-dioxide, 2-imino-9-trifluoromethyl-5,6-dihydro-2H,4H-thiazolo[3,4,5-ef][1,5]benzothiazepine, 2-imino-9-trifluoromethyl-4,5,6,7-tetrahydro-2H-thiazolo[5,4,3-jk][1]benzazepin-7-ol, 2-imino-9-trifluoromethoxy 4,5-dihydro-2H,7H-thiazolo[3,4,5-de][4,1]benzothiazepine 6,6-dioxide, 2-imino-9-trifluoromethoxy-4,5-dihydro-2H,7H-thiazolo[3,4,5-de][4,1]benzothiazepine 6-oxide, 6-benzyl-2-imino-9-trifluoromethyl-6,7-dihydro-4H-thiazolo[3,4.5-kj][1,4]benzodiazepin-5-one, 6-benzyl-2-imino-9-trifluoromethyl-4,5,6,7-tetrahydro-2H-thiazolo[3,4,5-kj][1,4]benzodiazepine, 2-imino-5-methyl-9-trifluoromethyl-4,5-dihydro-2H,7H-thiazolo[3,4,5-de][4,1]benzothiazepine, 5-carbamoyl-2-imino-9-trifluoromethyl-4,5-dihydro-2H,7H-thiazolo[3,4,5-de][4,1]benzothiazepine, 5,5-dimethyl-2-imino-9-trifluoromethyl-2H,4H,7H-thiazolo[3,4,5-de][4,1]benzothiazepine, 5-hydroxyethyl-2-imino-9-trifluoromethyl-4,5-dihydro-2H,7H-thiazolo[3,4,5-de)[4,1]benzothiazepine, and, when they contain one or more asymmetric centers, their isomers, racemates, enantiomers and their pharmaceutically acceptable salts with an inorganic or organic acid.

5. A compound of claim 1, selected from the group consisting of:

(R,S)-2-imino-9-trifluoromethyl-4,5-dihydro-2H,7H-thiazolo[3,4,5-de][4,1]benzothiazepine 6-oxide, (+)-2-imino-9-trifluoromethyl 4,5-dihydro-2H,7H-thiazolo[3,4,5-de][4,1]benzothiazepine 6-oxide, (−)-2-imino-9-trifluoromethyl-4,5-dihydro-2H,7H-thiazolo[3,4,5de][4,1]benzothiazepine 6-oxide, (R,S)-2-imino-5-methyl-9-trifluoromethyl-4,5-dihydro-2H,7H-thiazolo[3,4,5-de][4,1]benzothiazepine, (+)-2-imino-5-methyl-9-trifluoromethyl-4,5-dihydro-2H,7H-thiazolo[3,4,5-de][4,1]benzothiazepine, (−)-2-imino-5-methyl-9-trifluoromethyl-4,5-dihydro-2H,7H-thiazolo[3,4,5-de][4,1]benzothiazepine and their pharmaceutically acceptable salts with an inorganic or organic acid.

6. A process for the preparation of a compound of claim 1 wherein $R_1$ is a sulphur or selenium atom, $R_2$ is a hydrogen atom, —$R_3$—$R_4$—$R_5$—$R_6$— is a chain of formula —$CH_2$—$CH_2$—$CH_2$—$CH_2$—, —$CH_2$—$CH_2$—$CH_2$—$CO$—, —$CH_2$—$CH_2$—$CH_2$—$CH(R_8)$—, —$CH_2$—$CH_2$—$Se$—, —$CH_2$—$CH_2$—$Se$—$CH_2$—, —$CH_2$—$CH_2$—$CH_2$—$S$—, —$CH_2$—$CH_2$—$CH_2$—$O$—, —$CH_2$—$CH_2$—$CH_2$—$N(R_9)$—, —$CH_2$—$CH_2$—$CO$—$CH_2$—, —$CH_2$—$CH_2$—$CH(R_8)$—$CH_2$—, —$CH_2$—$CH_2$—$S$—$CH_2$—, —$CH_2$—$C(alk)(alk')$—$S$—$CH_2$—, —$CH_2$—$CH(R_{10})$—$S$—$CH_2$—, —$CH_2$—$CH_2$—$O$—$CH_2$—, —$CH_2$—$CH_2$—$N(R_9)$—$CH_2$— or —$CH_2$—$CO$—$N(R_9)$—$CH_2$—, $R_8$ is a hydroxyl radical, $R_9$ is a hydrogen atom or an alkyl or benzyl radical, $R_{10}$ is an alkyl, —$COOalk$, or —$CONH_2$ radical, alk is an alkyl radical and alk' is an alkyl radical, said process comprising reacting an alkali metal thiocyanate or alkali metal selenocyanate with a compound of formula:

(II)

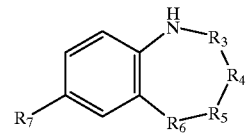

in which $R_7$ has the same meanings as in claim 1 and —$R_3$—$R_4$—$R_5$—$R_6$— is a chain of formula —$CH_2$—$CH_2$—$CH_2$—$CH_2$—, —$CH_2$—$CH_2$—$CH_2$—$CO$—, —$CH_2$—$CH_2$—$CH_2$—$CH(R_8)$—, —$CH_2$—$CH_2$—$CH_2$—$Se$—, —$CH_2$—$CH_2$—$Se$—$CH_2$—, —$CH_2$—$CH_2$—$CH_2$—$S$—, —$CH_2$—$CH_2$—$CH_2$—$O$—, $CH_2$—$CH_2$—$CH_2$—$N(R_9)$—, —$CH_2$—$CH_2$—$CO$—$CH_2$—, —$CH_2$—$CH_2$—$CH(R_8)$—$CH_2$—, —$CH_2$—$CH_2$—$S$—$CH_2$—, —$CH_2$—$C(alk)(alk')$—$S$—$CH_2$—, —$CH_2$—$CH(R_{10})$—$S$—$CH_2$—, —$CH_2$—$CH_2$—$O$—$CH_2$—, —$CH_2$—$CH_2$—$N(R_9)$—$CH_2$— or —$CH_2$—$CO$—$N(R_9)$—$CH_2$—, $R_8$ is a hydroxyl radical $R_9$ is a hydrogen atom or an alkyl or benzyl radical and $R_{10}$ is an alkyl, —$COOalk$ or —$CONH_2$ radical, alk is an alkyl radical and alkyl is an alkyl radical, and isolating the product and optionally converting it to a pharmaceutically acceptable salt of an inorganic or organic acid.

7. A process for the preparation of a compound according to claim 1 wherein $R_2$ represents an alkyl radical, which process comprises alkylating a compound of formula I in which $R_2$ is a hydrogen atom, isolating the product and optionally converting it to a pharmaceutically acceptable salt of an inorganic or organic acid.

8. A process for the preparation of a compound of claim 1 wherein $R_2$ is a hydrogen atom or an alkyl radical, —$R_3$—$R_4$—$R_5$—$R_6$— is a chain of formula —$CH_2$—$CH_2$—$CH(R_8)$—$CH_2$—or —$CH_2$—$CH_2$—$CH_2$—$CH(R_8)$— and $R_8$ is a hydroxyl radical, said process comprising reducing a compound of formula (I) wherein $R_2$ is a hydrogen atom or an alkyl radical and —$R_3$—$R_4$—$R_5$—$R_6$— is a chain of formula —$CH_2$—$CH_2$—$CO$—$CH_2$— or —$CH_2$—$CH_2$—$CH_2$—$CO$—, and isolating the product and optionally converting it to a pharmaceutically acceptable salt of an inorganic or organic acid.

9. A process for the preparation of a compound of claim 1 wherein $R_2$ is a hydrogen atom or an alkyl radical and —$R_3$—$R_4$—$R_5$—$R_6$— is a chain of formula —$CH_2$—$CH_2$—$CH_2$—$SO$—, —$CH_2$—$CH_2$—$CH_2$—$SO_2$—, —$CH_2$—$CH_2$—$SO$—$CH_2$—, —$CH_2$—$CH_2$—$SO_2$—$CH_2$—, —$CH_2$—$C(alk)(alk')$—$SO$—$CH_2$—, —$CH_2$—$C(alk)(alk')$—$SO_2$—$CH_2$—, —$CH_2$—$CH(R_{10})$—$SO$—$CH_2$— or —$CH_2$—$CH(R_{10})$—$SO_2$—$CH_2$—, said process comprising oxidizing a compound of formula (I) wherein —$R_3$—$R_4$—$R_5$—$R_6$— is a chain of formula —$CH_2$—$CH_2$—$CH_2$—$S$—, —$CH_2$—$CH_2$—$S$—$CH_2$—, —$CH_2$—$C(alk)(alk')$—$S$—$CH_2$—or —$CH_2$—$CH(R_{10})S$—$CH_2$— and isolating the product and optionally converting it to a pharmaceutically acceptable salt of an inorganic or organic acid.

10. A process for the preparation of a compound of claim 1 wherein $R_2$ is a hydrogen atom or an alkyl radical, and —$R_3$—$R_4$—$R_5$—$R_6$— is a chain of formula —$CH_2$—$CH(R_{10})$—S—$CH_2$— wherein $R_{10}$ is a —COOH radical, said process comprising hydrolysing a compound of formula (I) wherein $R_2$ is a hydrogen atom or an alkyl radical, and —$R_3$—$R_4$—$R_5$—$R_6$— is a chain of formula —$CH_2$—$CH(R_{10})$—S—$CH_2$— wherein $R_{10}$ is a —COOalk radical, and isolating the product and optionally converting it to a pharmaceutically acceptable salt of an inorganic or organic acid.

11. A compound of formula:

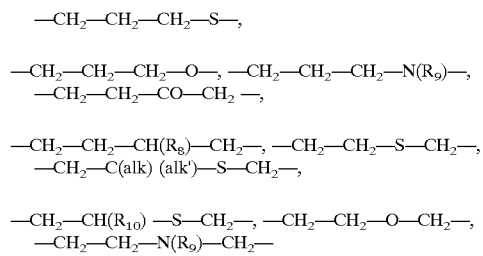

wherein —$R_3$—$R_4$—$R_5$—$R_6$— is a chain of formula

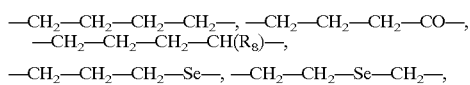

—$CH_2$—$CH_2$—$CH_2$—S—,

—$CH_2$—$CH_2$—$CH_2$—O—, —$CH_2$—$CH_2$—$CH_2$—$N(R_9)$—,
—$CH_2$—$CH_2$—CO—$CH_2$—,

—$CH_2$—$CH_2$—$CH(R_8)$—$CH_2$—, —$CH_2$—$CH_2$—S—$CH_2$—,
—$CH_2$—C(alk)(alk')—S—$CH_2$—, —$CH_2$—$CH(R_{10})$—S—$CH_2$—, —$CH_2$—$CH_2$—O—$CH_2$—,
—$CH_2$—$CH_2$—$N(R_9)$—$CH_2$— or

—$CH_2$—CO—$N(R_9)$—$CH_2$—, $R_7$ is a polyfluoroalkyl or polyfluoroalkoxy radical, $R_8$ is a hydroxyl radical, $R_9$ is a hydrogen atom or an alkyl or benzyl radical, $R_{10}$ is an alkyl, —COOalk or —$CONH_2$ radical, alk is an alkyl radical and alk' is an alkyl radical, the alkyl radicals containing 1 to 6 straight- or branched-chain carbon atoms.

* * * * *